United States Patent
Weinberg et al.

(10) Patent No.: US 10,082,515 B2
(45) Date of Patent: Sep. 25, 2018

(54) PEPTIDE-LIPID CONSTRUCTS AND THEIR USE IN DIAGNOSTIC AND THERAPEUTIC APPLICATIONS

(71) Applicant: Kode Biotech Limited, Auckland (NZ)

(72) Inventors: Cristina-Simona Weinberg, Waitakere City (NZ); Nicolai Bovin, Moscow (RU); Stephen Micheal Henry, Auckland (NZ)

(73) Assignee: KODE BIOTECH LIMITED, Auckland (NZ)

( * ) Notice: Subject to any disclaimer, the term of this patent is extended or adjusted under 35 U.S.C. 154(b) by 330 days.

(21) Appl. No.: 13/765,314

(22) Filed: Feb. 12, 2013

(65) Prior Publication Data

US 2013/0280746 A1 Oct. 24, 2013

Related U.S. Application Data

(63) Continuation of application No. 12/733,593, filed as application No. PCT/NZ2008/000239 on Sep. 11, 2008, now Pat. No. 8,394,594.

(30) Foreign Application Priority Data

Sep. 11, 2007 (NZ) ........................ 561381
Oct. 12, 2007 (NZ) ........................ 562476
Jun. 6, 2008 (NZ) ........................ 569023

(51) Int. Cl.
*G01N 33/92* (2006.01)
*C07F 9/09* (2006.01)
*C07F 9/572* (2006.01)
*C07K 5/103* (2006.01)
*C07K 14/47* (2006.01)
*C07K 17/08* (2006.01)
*C12N 5/00* (2006.01)
*C12N 5/078* (2010.01)
*G01N 33/555* (2006.01)
*G01N 33/68* (2006.01)
*G01N 33/53* (2006.01)
*G01N 33/554* (2006.01)
*G01N 33/80* (2006.01)
*A61K 47/54* (2017.01)

(52) U.S. Cl.
CPC ........... *G01N 33/92* (2013.01); *A61K 47/543* (2017.08); *A61K 47/544* (2017.08); *C07F 9/091* (2013.01); *C07F 9/5721* (2013.01); *C07K 5/1008* (2013.01); *C07K 14/47* (2013.01); *C07K 17/08* (2013.01); *C12N 5/0006* (2013.01); *C12N 5/0641* (2013.01); *G01N 33/5304* (2013.01); *G01N 33/554* (2013.01); *G01N 33/555* (2013.01); *G01N 33/6854* (2013.01); *G01N 33/80* (2013.01); *C12N 2503/00* (2013.01); *G01N 2405/00* (2013.01)

(58) Field of Classification Search
CPC ...... C07F 9/091; C07F 9/5721; C07K 5/1008; C07K 14/47; C07K 17/08; C12N 5/0006; C12N 5/0641; C12N 2503/00; G01N 33/555; G01N 33/6854; G01N 33/92; G01N 33/5304; G01N 33/554; G01N 33/80; G01N 2405/00; A61K 47/543; A61K 47/544

See application file for complete search history.

(56) References Cited

U.S. PATENT DOCUMENTS 6,521,211 B1 2/2003 Unger et al.
7,153,933 B2 12/2006 Wu et al.

FOREIGN PATENT DOCUMENTS

WO WO 00/45856 8/2000

OTHER PUBLICATIONS

Zalipsky et al. Functionalized poly(ethylene glycol) for preparation of biologically relevant conjugates. Bioconjugate Chem. 1995, vol. 6, pp. 150-165.*
Lestini et al. Surface modification of liposomes for selective cell targeting in cardiovascular drug delivery. Jorrnal of controlled release, 2002, vol. 78, pp. 235-247.*
Schelté. P., et al; "Differential Reactivity of Maleimide and Bromoacetyl Functions with Thiols: Application to the Preparation of Liposomal Diepitope Constructs"; *Bioconjugate Chemistry* (2000) 11 (1): 118-123.

* cited by examiner

*Primary Examiner* — Shafiqul Haq
(74) *Attorney, Agent, or Firm* — Nixon & Vanderhye P.C.

(57) ABSTRACT

Method of incorporating a water soluble construct of the structure L-S-F into the lipid bi-layer of cells by contacting a suspension of the cells with a solution of the construct at a concentration and for a time and temperature sufficient to allow the construct to insert into the lipid bi-layer. In the structure L-S-F, F is a peptide, S is a spacer containing an oligomer of ethylene glycol covalently linking F to L and the number of ethylene oxide repeats in the oligomer of ethylene glycol is 6 to 14, and L is a phosphatidylethanolamine.

5 Claims, 5 Drawing Sheets
Specification includes a Sequence Listing.

PEPTIDE-LIPID CONSTRUCTS AND THEIR USE IN DIAGNOSTIC AND THERAPEUTIC APPLICATIONS

This is a continuation of application Ser. No. 12/733,593 filed Oct. 28, 2010, U.S. Pat. No. 8,394,594, which is the National Phase of PCT/NZ2008/000239 filed Sep. 11, 2008, which claims priority to New Zealand Patent Application No. 561381 filed Sep. 11, 2007, New Zealand Patent Application No. 562476 filed Oct. 12, 2007, and New Zealand Patent Application No. 569023 filed Jun. 6, 2008, the entire contents of each of which are hereby incorporated by reference.

TECHNICAL FIELD

The invention relates to methods for effecting qualitative and quantitative changes in the levels of peptide expressed at the surface of cells and multi-cellular structures, and constructs for use in such methods.

In particular, the invention relates to peptide-lipid constructs for use in diagnostic and therapeutic applications, including serodiagnosis.

BACKGROUND ART

The ability to effect qualitative and quantitative changes in the level of peptides expressed at the surface of cells and multi-cellular structures provides for a range of diagnostic and therapeutic applications.

Qualitative and quantitative changes in the level of peptides expressed at the surface may modify trans-membrane transport, cell-solute and cell-cell interactions, and thus the functionality of the modified cell or multi-cellular structure.

Known methods of effecting such changes include gene manipulation, chemical modification of endogenous membrane peptides, and "cell surface painting" using lipid anchors such as GPI.

The specification accompanying international application number PCT/NZ2005/000052 (publication number WO 2005/090368) describes the preparation of water soluble carbohydrate-lipid constructs for use in methods of effecting qualitative and quantitative changes in the level of carbohydrates expressed at the surface of cells and multicellular structures.

The specification accompanying international application number PCT/NZ2006/000245 (publication number WO 2007/035116) describes another method for the preparation of water soluble carbohydrate-lipid constructs where the carbohydrate is the polymer hyaluronic acid. Use of the construct to modify embryos and promote association with endometrial cells is described.

Relatively little work has been performed on the site-directed coupling of peptides to phospholipids as individual components prior to their incorporation in self assembling lipid structures, such as liposomes, or as would be required to provide peptide-lipid constructs for use in methods of effecting qualitative and quantitative changes in the level of peptide expressed at the surface of cells and multicellular structures.

A variety of standard techniques have been described for the covalent coupling of peptides to liposomes surfaces.

Martin at al (1990) has reviewed methods of attaching moieties including peptides, to the surface of liposomes.

Blume at al (1993) describes the coupling of the water soluble Glu-plasminogen to liposomes by the method described by Kung and Redemann (1986). The chemical ECDI (1-ethyl-(3-dimethylaminopropyl)carbodiimide hydrochloride) is used to activate the liposomes prior to incubation of the activated liposome suspension with Glu-plasminogen. Proteo-PEG-coated liposomes with Glu-plasminogen covalently attached to the ends of the distearylyphosphatidylethanolamine (DSPE)-PEG-COOH are provided.

Haselgrübler et al (1995) describes a heterobifunctional crosslinker used to facilitate the preparation of immunoliposomes. The crossllinker is synthesised from a diamine derivative of poly(ethylene glycol) (PEG, average molecular weight 800 dalton (18mer)). The crosslinker has 2-(pyridylthio)propronyl (PDP) and N-hydroxysuccinimide ester (NHS) as functional groups.

Ishida et al (2001) describes the preparation of liposomes bearing polyethylene glycol-coupled transferrin. Transferrin was conjugated via the terminal carboxyl residue of DSPE-PEG-COOH. The liposomes were proposed as having utility in in vivo cytoplasmic targeting of chemotherapeutic agents or plasmid DNAs to target cells.

Massaguer et al (2001) describes the incorporation of a peptide sequence (GGRGRS) and hydrophobic derivatives to the surface of chemically activated liposomes. The incorporation was carried out through the carboxyl group of N-glutaryl dipalmitoyl phosphatidyl choline (NGPE).

Massaguer et al (2001) noted that considering potential in vivo applications, where sterility and simplicity would be some of the most important requirements, processes based on chemical reactions on the surface of liposomes involving extra steps would be more difficult to be scaled up at the industrial level. A hydrophobic derivative of the peptide sequence was identified as providing optimal properties for incorporation to the surface of liposomes.

Chung et al (2004) describe the antigenic determinant shielding effect of DOPE-PEG incorporated into the membranes of cells and speculated concerning the potential of lipid-PEG(n)(s) to regulate biological cell responses and the extension of this concept to the introduction of functional molecules at the end of the PEG chain.

Kato et al (2004) describe a method for anchoring of macromolecular proteins into the membranes of living mammalian cells. A dioleylphosphatidylethanolamine (DOPE) derivative coupled with hydrophilic poly(ethylene glycol) (PEG80) was used as the synthetic membrane anchor. Peptides were conjugated at the distal terminal of the PEG moiety via an amino-reactive N-hydroxysuccinimide derivative of the synthetic membrane anchor.

The PEG80 moiety facilitated soulbilisation of the synthetic membrane anchor in water. As noted by Kato et al (2004) if the anchor is insoluble in water, undesirable and complicated processes such as liposome preparation and the fusion of liposomes with the cell membrane may be required to anchor the conjugates into the cell membrane.

An additional advantage noted by Kato et al (2004) was that synthetic membrane anchors with high hydrophile-lipophile balance values (attributable to PEG spacer with a high number of oxyethylene units) were concluded to have no cytolytic activity. However, difficulties arise in the use of synthetic membrane anchors including a PEG spacer with a high number of oxyethylene units.

Firstly, the expression of the conjugative peptide or other endogenous cell surface peptides may be masked by the PEG spacer. Secondly, a PEG spacer with a high number of oxyethylene units may elicit non-specific adherence of protein (including antibodies in certain individuals) and/or the non-specific activation of the complement cascade.

Winger et al (1996) describes the conjugation of bromoacetylated DSPE with a thiol terminated decapeptide comprising at its C-terminus the minimal human thrombin-receptor peptide agonist (HS-SerPheLeuLeuArgAsn).

Hashimoto et al (1986) describes the conjugation of iodoacetylated DSPE with thiolated compounds.

A need exists for peptide-lipid constructs that can be used to effect qualitative and quantitative changes in the level of peptides expressed at the surface of cells and multi-cellular structures.

It is an object of this invention to provide peptide-lipid constructs that satisfy this need or at least provide a useful choice.

DISCLOSURE OF INVENTION

In a first aspect the invention provides a method of detecting reactive antibody in the serum of a subject including the steps of:

Contacting a sample of the serum with a suspension of cells modified to incorporate a peptide-lipid construct of the structure $(L-S-)_iF(-S-L)_j$ to provide a mixture;

Incubating the mixture for a time and at a temperature sufficient to allow agglutination; and Determining the degree of agglutination of the cells in the mixture;

where:

F is a peptide comprising an epitope for the reactive antibody;

S is a spacer covalently linking F to L; and

L is a lipid selected from the group consisting of diacyl- and dialkyl-glycerolipids, including glycerophospholipids; and i and j are independently 0 or 1, Optionally, the method includes the preliminary step of:

Adding an amount of the peptide to the sample of the serum;

where the amount of the peptide is sufficient to neutralize non-specific agglutination or confirm specificity of the reactive antibody.

Optionally, the method includes the intermediate step of:

Adding an anti-subject globulin antibody to the mixture prior to determining the degree of agglutination of the cells of the mixture.

Preferably, the subject is a human.

Preferably, the cells are red blood cells.

Preferably, the anti-subject globulin antibody is anti-human globulin (AHG) antibody.

Preferably, the reactive antibody is reactive to an antigen selected from the group consisting of: Glycophorin A, Glycophorin B, or mutations thereof (including the MNS blood group system).

The spacer (S) is selected to provide a water soluble peptide-lipid construct.

Preferably, S is a spacer covalently linking F to L via an oligomer of ethylene glycol.

Preferably, the structure of the peptide-lipid construct includes the substructure:

where M is a monovalent cation ($M^+$), n is 6 to 14 and * is other than H.

More preferably, the structure of the peptide-lipid construct is either:

where M is a monovalent cation ($M^+$), n is 6 to 14, w is 1 or 2, the sum of x and y is greater than 5, z is greater than 5, and * is other than H.

Preferably, the sum of i and j is 1.

Optionally, F is a peptide including a proximal terminal sequence (PTS) selected to promote solubility of the peptide.

In a preferment of this option, the PTS of the peptide is selected from the group consisting of:

```
SerLysLysLysLysGly

AlaAlaAlaAla

GlySerGlySerGly
```

Preferably, F is a peptide comprising an epitope of antigens selected from the group consisting of: Glycophorin A, Glycophorin B, or mutations thereof (including the MNS blood group system).

More preferably, F is a peptide selected from the List of Peptides.

Most preferably, F is a peptide selected from the group consisting of:

GlnThrAsnAspLysHisLysArgAspThrTyrAlaAlaAlaAlaAlaCys

GlnThrAsnAspLysHisLysArgAspThrTyrGlySerGlySerGlyCys

GlnThrAsnAspMetHisLysArgAspThrTyrGlySerGlySerGlyCys

SerSerGlnThrAsnAspLysHisLysArgAspThrTyrCys

ThrTyrProAlaHisThrAlaAsnGluValCys

ProAlaHisThrAlaAsnGluValCys

SerGlnThrAsnAspLysHisLysArgAspCys

AlaAlaAlaAlaValMetTyrAlaSerSerGly

GlySerGlySerGlyValMetTyrAlaSerSerGly

Preferably, L is a glycerophospholipid. More preferably, L is a glycerophospholipid selected from the group consisting of: 1,2-O-dioleoyl-sn-glycero-3-phosphatidylethanolamine (DOPE) and 1,2-O-distearyl-sn-glycero-3-phosphatidylethanolamine (DSPE).

Preferably, the peptide-lipid construct is an exemplifying embodiment of the second or third aspect of the invention.

In a second aspect the invention provides a peptide-lipid construct of the structure:

L-S-F where

F is a peptide;

S is a spacer covalently linking F to L via an oligomer of ethylene glycol; and

L is a lipid selected from the group consisting of diacyl- and dialkyl-glycerolipids, including glycerophospholipids.

Preferably, the structure of the peptide-lipid construct includes the substructure:

where M is a monovalent cation (M⁺), n is 6 to 14 and * is other than H.

Optionally, F is a peptide including a proximal terminal sequence (PTS) selected to promote solubility of the peptide.

In a preferment of this option, the PTS of the peptide is selected from the group consisting of:

SerLysLysLysLysGly

AlaAlaAlaAla

GlySerGlySerGly

Preferably, the terminal sequence of the peptide is selected from the group consisting of:

GlyLysLysLysLysSerCys

AlaAlaAlaAlaCys

GlySerGlySerGlyCys

CysSerLysLysLysLysGly

CysAlaAlaAlaAla

CysGlySerGlySerGly

Preferably, S is covalently linked to F via a sulphide bond formed with the Cys residue of the peptide.

More preferably, S is covalently linked to F via a sulphide bond formed with a Cys residue of the peptide at or proximal to a terminus of the peptide.

Most preferably, S is linked to F via a sulphide bond formed with a Cys residue of the peptide at the carboxy-terminus of the peptide.

The spacer (S) is of the structure $S_1$-$S_2$-$S_3$ and selected to provide a water soluble construct. $S_1$ is an oligomer of ethylene glycol.

Preferably, $S_2$-$S_3$ is selected from the group consisting of:

where $R_1$ is a terminal carbon of $S_1$, $R_2$ is the sulphur of the Cys residue and w is 1 or 2.

Preferably, the structure of the peptide-lipid construct is:

where M is a monovalent cation ($M^+$), n is 6 to 14, w is I or 2, the sum of x and y is greater than 5, and X is other than H. More preferably, n is 6. Most preferably, y is 0.

Preferably, F is a peptide comprising an epitope of antigens selected from the group consisting of: Glycophorin A, Glycophorin B, or mutations thereof (including the MNS blood group system).

More preferably, F is a peptide selected from the List of Peptides.

Most preferably, F is a peptide selected from the group consisting of:

GlnThrAsnAspLysHisLysArgAspThrTyrAlaAlaAlaAlaAlaCys

GlnThrAsnAspLysHisLysArgAspThrTyrGlySerGlySerGlyCys

-continued

GlnThrAsnAspMetHisLysArgAspThrTyrGlySerGlySerGlyCys

SerSerGlnThrAsnAspLysHisLysArgAspThrTyrCys

ThrTyrProAlaHisThrAlaAsnGluValCys

ProAlaHisThrAlaAsnGluValCys

SerGlnThrAsnAspLysHisLysArgAspCys

Preferably, L is a glycerophospholipid. More preferably, L is a glycerophospholipid selected from the group consisting of: 1,2-O-dioleoyl-sn-glycero-3-phosphatidylethanolamine (DOPE) and 1,2-O-distearyl-sn-glycero-3-phosphatidylethanolamine (DSPE).

In an exemplifying first embodiment of the second aspect the invention provides a peptide-lipid construct of the structure:

GlnThrAsnAspLysHisLysArgAspThrTyrAlaAlaAlaAlaAlaCys 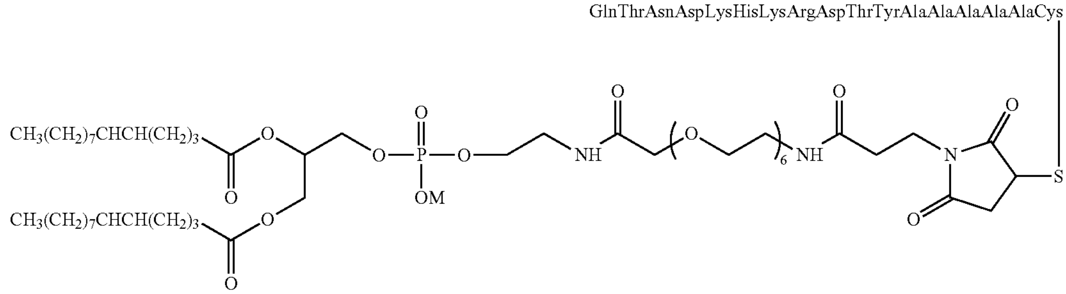 where M is a monovalent cation ($M^+$) and designated DOPE-PEG$_6$-βAla-Mal-PTS-1MUTK)(M1).

In an exemplifying second embodiment of the second aspect the invention provides a peptide-lipid construct of the structure:

GlnThrAsnAspLysHisLysArgAspThrTyrGlySerGlySerGlyCys 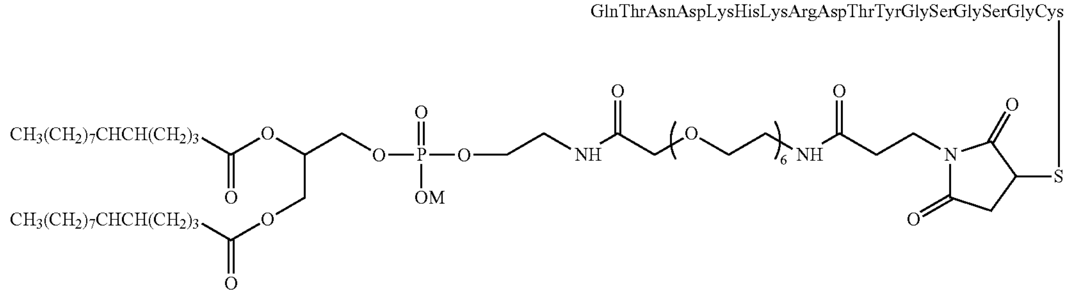 where M is a monovalent cation ($M^+$) and designated DOPE-PEG$_6$-βAla-Mal-PTS-2MUTK)(M2).

In an exemplifying third embodiment of the second aspect the invention provides a peptide-lipid construct of the structure:

GlnThrAsnAspMetHisLysArgAspThrTyrGlySerGlySerGlyCys where M is a monovalent cation (M⁺) and designated DOPE-PEG$_6$-βAla-Mal-PTS-3MUTM(M3).

In an exemplifying fourth embodiment of the second aspect the invention provides a peptide-lipid construct of the structure:

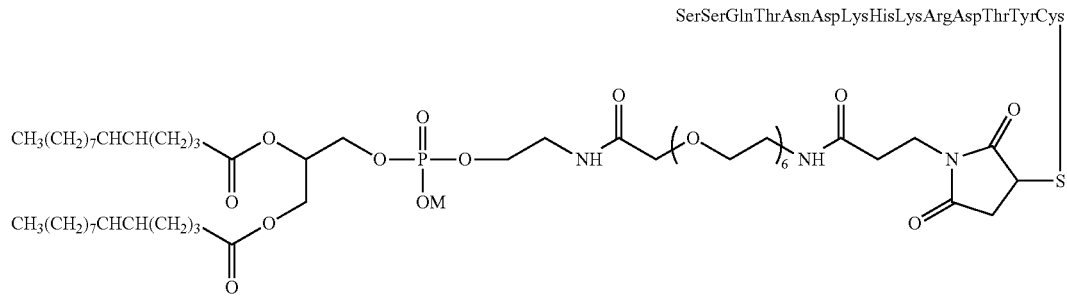

where M is a monovalent cation (M⁺) and designated DOPE-PEG$_6$-βAla-Mal-13MUTK(M13).

In an exemplifying fifth embodiment of the second aspect the invention provides a peptide-lipid construct of the structure:

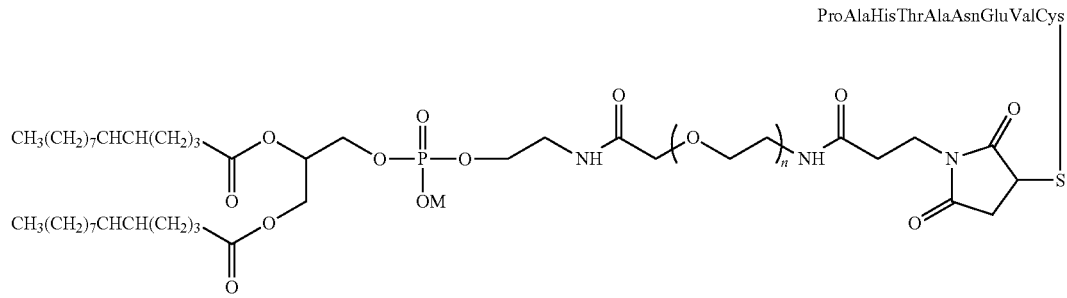

where M is a monovalent cation (M⁺) and designated DOPE-PEG$_6$-βAla-Mal-18Mur (M18) (n=6).

In an exemplifying sixth embodiment of the second aspect the invention provides a peptide-lipid construct of the structure:

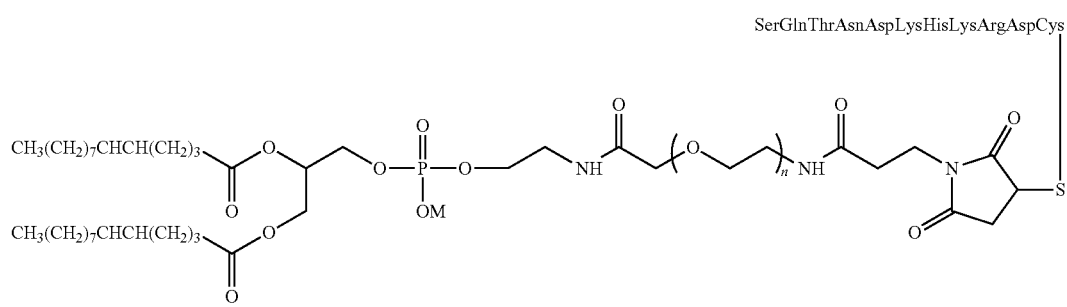

where M is a monovalent cation (M⁺) and designated DOPE-PEG$_6$-βAla-Mal-21MUTK(M21) (n=6).

In an exemplifying seventh embodiment of the second aspect the invention provides a peptide-lipid construct of the structure:

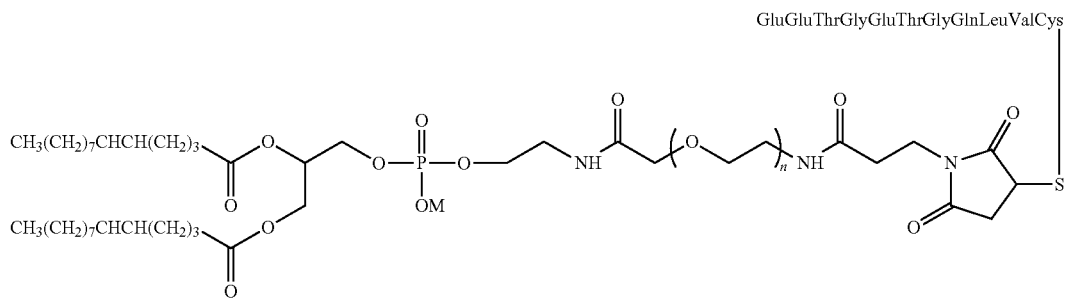

where M is a monovalent cation (M$^+$) and designated DOPE-PEG$_6$-βAla-Mal-Hil3(M23) (n=6).

In an exemplifying eighth embodiment of the second aspect the invention provides a peptide-lipid construct of the structure:

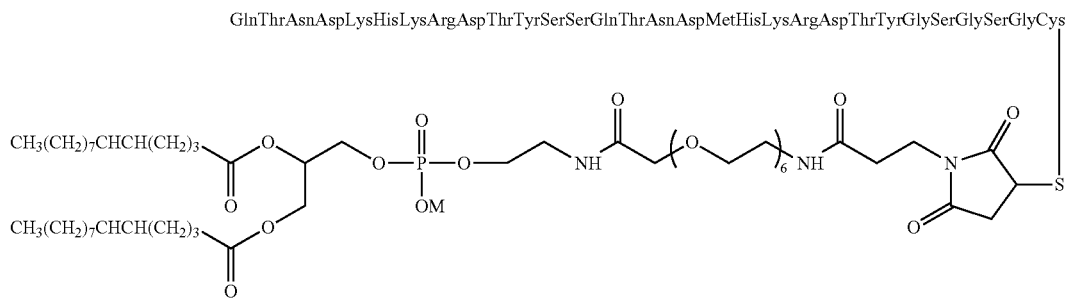

where M is a monovalent cation (M$^+$) and designated DOPE-PEG$_6$-βAla-Mal-PTS-Milt(K,M).

In an exemplifying ninth embodiment of the second aspect the invention provides a peptide-lipid construct of the structure:

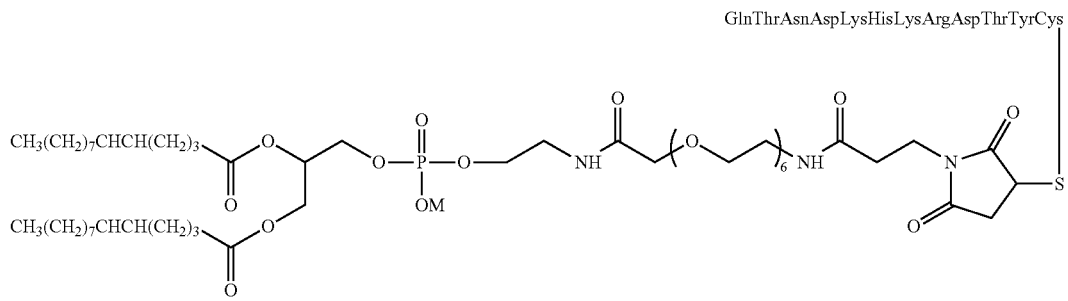

where M is a monovalent cation (M$^+$) and designated DOPE-PEG$_6$-βAla-Mal-Milt(K) (M00).

In an exemplifying tenth embodiment of the second aspect the invention provides a peptide-lipid construct of the structure:

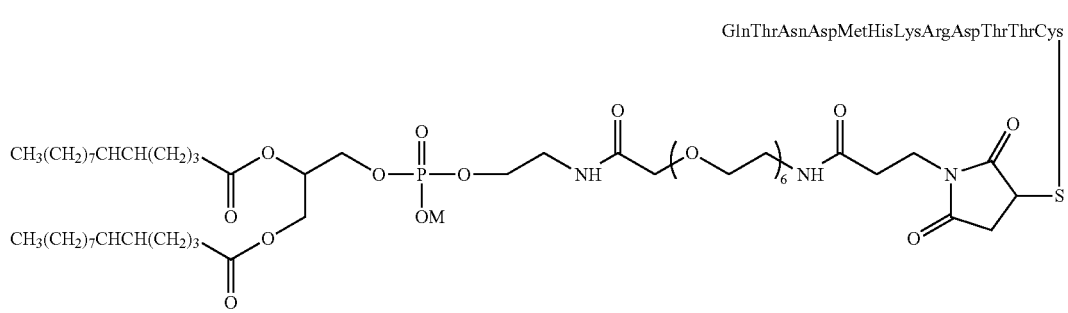

where M is a monovalent cation (M⁺) and designated DOPE-PEG$_6$-βAla-Mal-Milt(M).

In an exemplifying eleventh embodiment of the second aspect the invention provides a peptide-lipid construct of the structure:

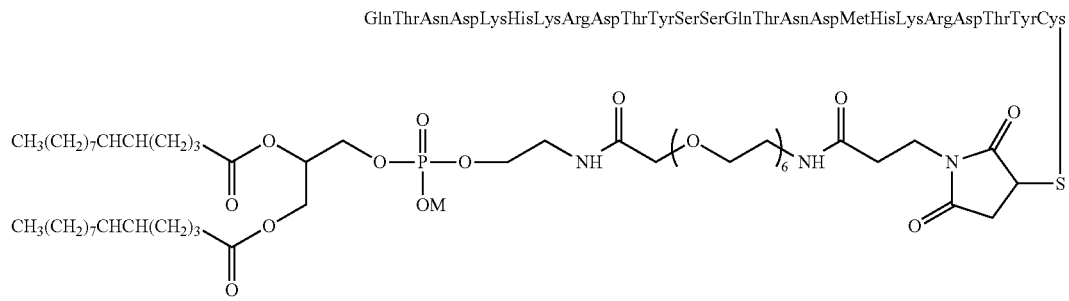

where M is a monovalent cation (M⁺) and designated DOPE-PEG$_6$-βAla-Mal-Milt(K,M).

In a third aspect the invention provides a peptide-lipid construct of the structure:

L-S-F where
- F is a peptide;
- S is a spacer covalently linking F to L via an oligomer of ethylene glycol; and
- L is a lipid selected from the group consisting of diacyl- and dialkyl-glycerolipids, including glycerophospholipids.

Preferably, the structure of the peptide-lipid construct is:

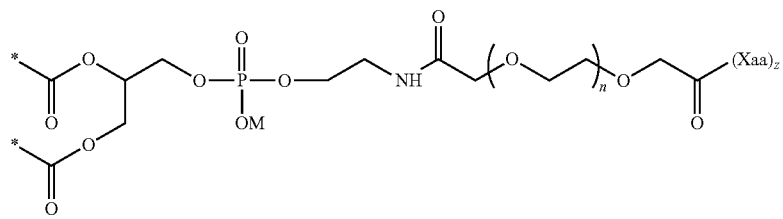

where M is a monovalent cation (M⁺), n is 6 to 14, z is greater than 5, and * is other than H. More preferably, n is 14.

Optionally, F is a peptide including a terminal sequence selected to promote solubility of the peptide.

In a preferment of this option, the terminal sequence of the peptide is selected from the group consisting of:

```
SerLysLysLysLysGly

AlaAlaAlaAla

GlySerGlySerGly
```

Preferably, a peptide selected from the group consisting of:

```
(Xaa)_zValMetTyrAlaSerSerGly;
``` where z is the integer 4, 5 or 6.

Preferably, F is a peptide selected from the group consisting of:

```
SerLysLysLysLysGlyValMetTyrAlaSerSerGly

AlaAlaAlaAlaValMetTyrAlaSerSerGly

GlySerGlySerGlyValMetTyrAlaSerSerGly
```

Preferably, L is a glycerophospholipid. More preferably, L is a glycerophospholipid selected from the group consisting of: 1,2-O-dioleoyl-sn-glycero-3-phosphatidylethanolamine (DOPE) and 1,2-O-distearyl-sn-glycero-3-phosphatidylethanolamine (DSPE).

In an exemplifying first embodiment of the third aspect the invention provides a peptide-lipid construct of the structure:

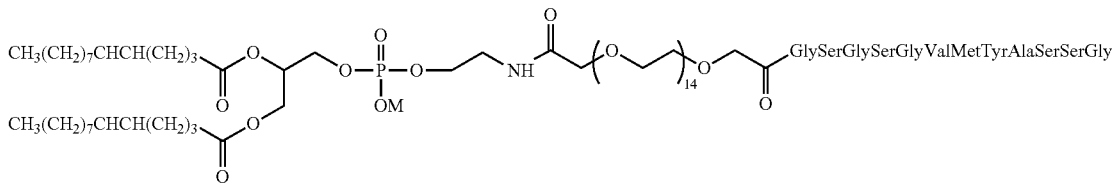

where M is a monovalent cation (M⁺) and designated DOPE-PEG$_{14}$-Syph.

In a fourth aspect the invention provides a method of preparing a peptide-lipid construct (F-S-L) of the second aspect of the invention including the steps of:

Preparing a maleimido-derivative of a precursor construct by reacting a maleimido-donating reagent with a precursor construct of the structure L-S$_1$-NH$_2$; and Reacting the maleimido-derivative of the precursor construct with a peptide (F) including a Cys residue and solubilised in a solvent.

where:
L is a lipid selected from the group consisting of diacyl- and dialkyl-glycerolipids, including glycerophospholipids; and
S$_1$ is selected from the group consisting of oligomers of ethylene glycol.

Preferably, the structure of the peptide-lipid construct is:

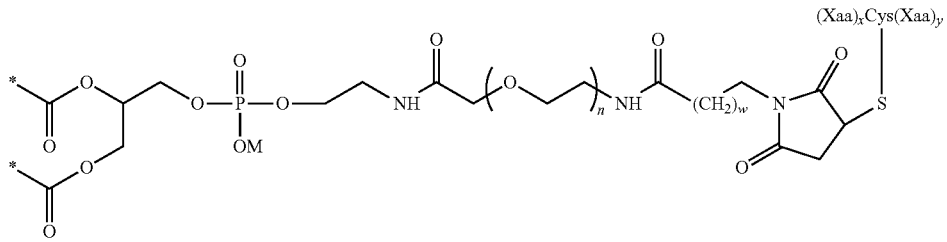

where n is 6 to 14, w is 1 or 2, the sum of x and y is greater than 5, and * is other than H.

Preferably the maleimido-donating reagent is selected from the group consisting of: N-oxysuccinimid ester of maleimidobutyric acid; and N-oxysuccinimid ester of maleimidopropionic acid Preferably, S$_1$ is an oligomer of ethylene glycol selected from the group consisting of 6 to 14 mer PEG (PEG$_6$ to PEG$_{14}$). Most preferably, S$_1$ is PEG$_6$.

Preferably, the solvent is selected from the group consisting of: trifluoroethanol; DMSO; or mixtures thereof.

Preferably, the Cys residue is a terminal Cys residue.

Optionally, F is a peptide including a proximal terminal sequence (PTS) selected to promote solubility of the peptide in the reaction solvent.

In a preferment of this option, the PTS of the peptide is selected from the group consisting of:

```
SerLysLysLysLysGly

AlaAlaAlaAla

GlySerGlySerGly
```

Preferably, the terminal sequence of the peptide is selected from the group consisting of:

```
GlyLysLysLysLysSerCys

AlaAlaAlaAlaCys

GlySerGlySerGlyCys

CysSerLysLysLysLysGly

CysAlaAlaAlaAla

CysGlySerGlySerGly
```

Preferably, F is a peptide selected from the List of Peptides.

Preferably, F is a peptide selected from the group consisting of:

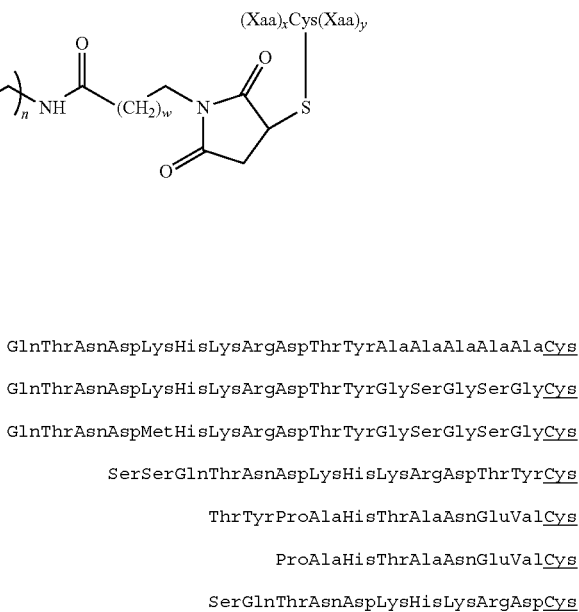

```
GlnThrAsnAspLysHisLysArgAspThrTyrAlaAlaAlaAlaAlaCys

GlnThrAsnAspLysHisLysArgAspThrTyrGlySerGlySerGlyCys

GlnThrAsnAspMetHisLysArgAspThrTyrGlySerGlySerGlyCys

SerSerGlnThrAsnAspLysHisLysArgAspThrTyrCys

ThrTyrProAlaHisThrAlaAsnGluValCys

ProAlaHisThrAlaAsnGluValCys

SerGlnThrAsnAspLysHisLysArgAspCys
```

Preferably, L is a glycerophospholipid. More preferably, L is a glycerophospholipid selected from the group consisting of: 1,2-O-dioleoyl-sn-glycero-3-phosphatidylethanolamine (DOPE) and 1,2-O-distearyl-sn-glycero-3-phosphatidylethanolamine (DSPE).

In a fifth aspect the invention provides a method of effecting qualitative and quantitative changes in the levels of peptide expressed at the surface of cells and multi-cellular structures including the step of;

contacting the cells or multi-cellular structures with a solution of a peptide-lipid construct of the second or third aspects of the invention at a concentration and for a time and temperature sufficient to allow the construct to incorporate into the surface.

Preferably, the peptide-lipid construct is a construct of the second aspect of the invention.

Preferably the cells or multicellular structures are selected from the group consisting of: red blood cells; and embryos. More preferably, the cells or multicellular structures are human cells on multicellular structures.

Preferably, the time and temperature is no greater than 2 hours at 37° C. or 24 hours at 4° C.

In all aspects of the invention M is typically H, but may be replaced by another monovalent cation such as $Na^+$, $K^+$ or $NH_4^+$.

In the description and claims of the specification the following acronyms, phrases and terms have the meaning provided:

"Diagnostic marker" means a molecule, the presence of which in a body fluid of a subject is diagnostic of a phenotype or pathological condition of the subject.

"MNS blood group system" means blood group antigens or epitopes of those antigens and mutations which are present on either glycophorin A, glycophorin B or mutations which result in glycophorin A/B hybrids.

"Proximal terminal sequence" means that portion of the peptide sequence proximal to the amino- or carboxy-terminus of the peptide (F).

"RBC" means red blood cells.

"Reactive antibody" means an immunoglobulin, the presence of which in a body fluid of a subject is diagnostic of a phenotype or pathological condition of the subject.

"Via an oligomer of ethylene glycol" means a polymer of ethylene glycol consisting of 2 to 32 mer and specifically excludes via a polymer of ethylene glycol consisting of greater than 32 mer.

"Water soluble" means a stable, single phase system is formed when the construct is contacted with water or saline (such as PBS) at a concentration of at least 100 μg/ml and in the absence of organic solvents or detergents. The phrase is used synonymously with the term "water dispersible".

Exemplifying embodiments of the invention are claimed and will now be described in detail with reference to the Figures of the accompanying drawings pages.

DETAILED DESCRIPTION

Figure 1:
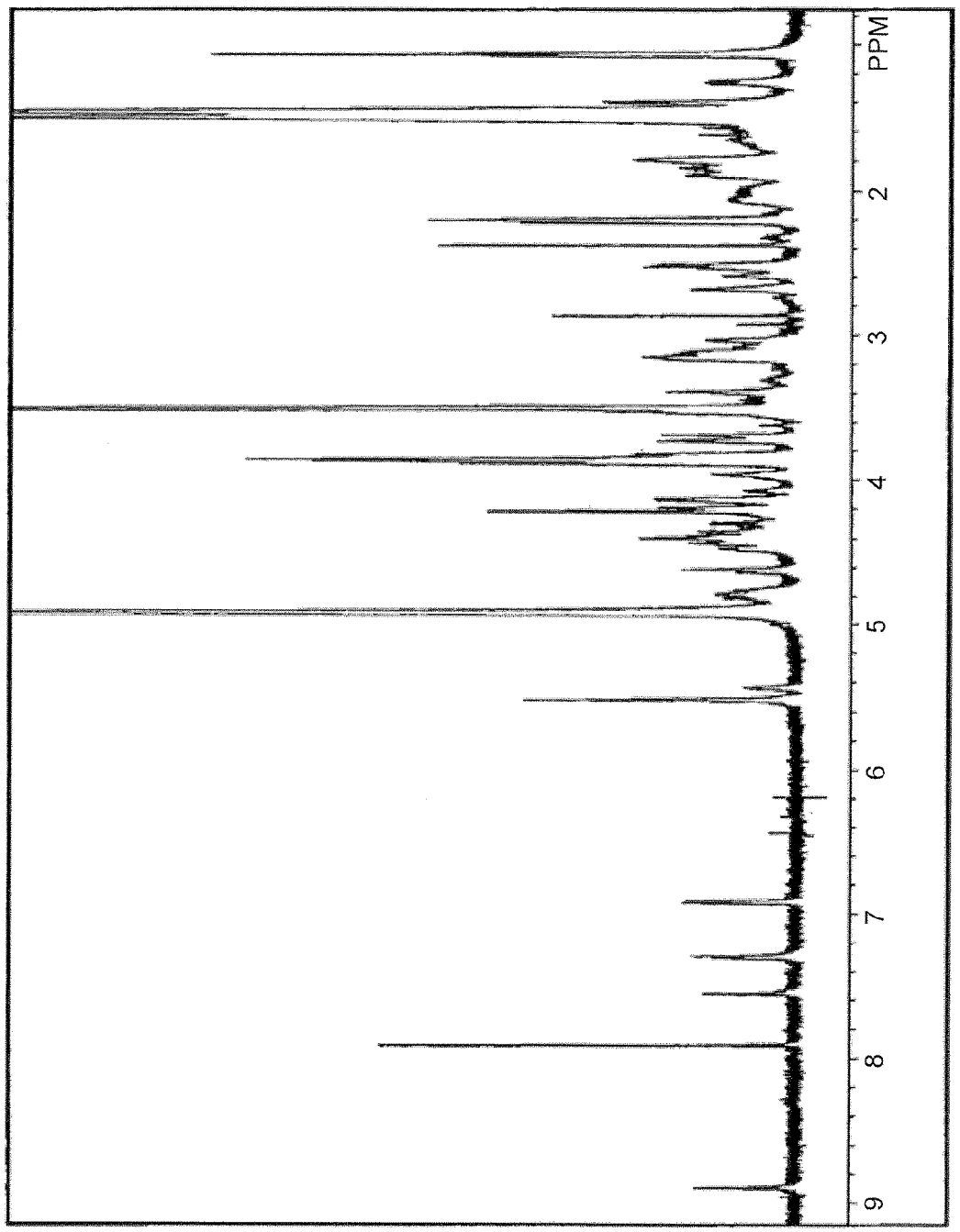
FIG. 1, $^1$H-NMR spectrum of the peptide-lipid construct designated DOPE-PEG$_6$-βAla-Mal-Milt(K)(M13) (5 mg/ml in CD$_3$OD/CDCl$_3$/D$_2$O/0.5M CF$_3$COOD 60/20/10/1, 600 MHz, 30° C., δ ppm).
Figure 2:
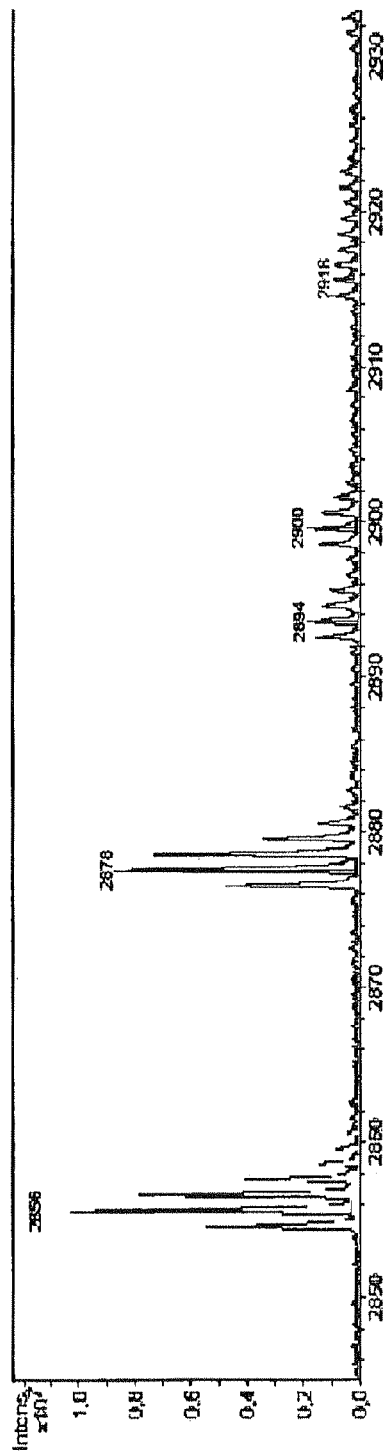
FIG. 2. MALDI TOF mass-spectrum of the peptide-lipid construct designated DOPE-PEG$_6$-βAla-Mal-Milt(K)(M13) (2856:Peptide-DOPE (M+H); 2878: Peptide-DOPE (M+Na); 2894:Peptide-DOPE (M+K); 2900:Peptide-DOPE (M+Na, Na salt); 2916:Peptide-DOPE (M+K, Na salt)).
Figure 3:
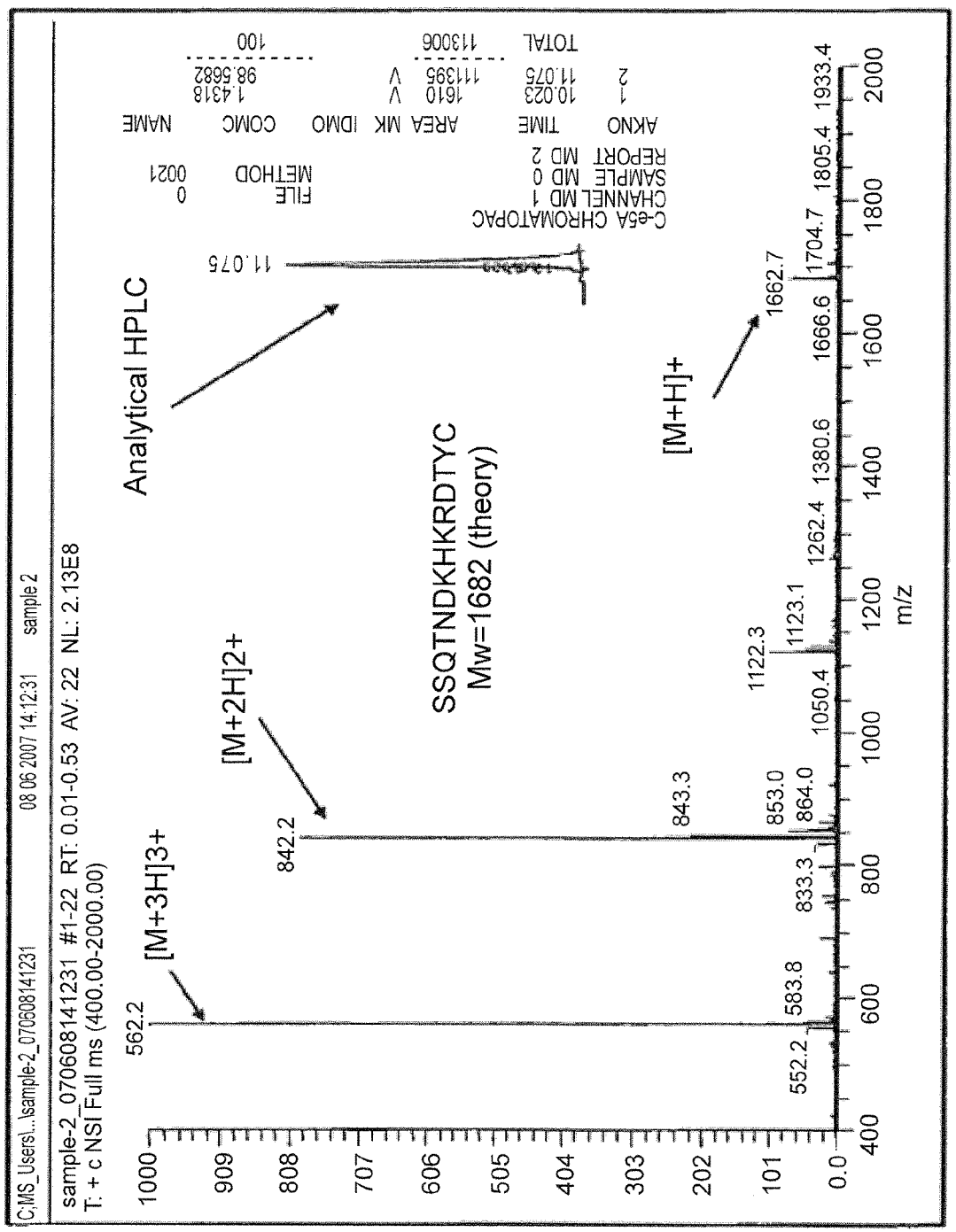
FIG. 3. ESI mass-spectrum and analytical HPLC of the peptide SerSerGlnThrAsnAspLysHisLysArgAspThrTyrGlySerGlySerGlyCys of the peptide-lipid construct designated DOPE-PEG$_6$-βAla-Mal-Milt(K)(M13).
Figure 4:
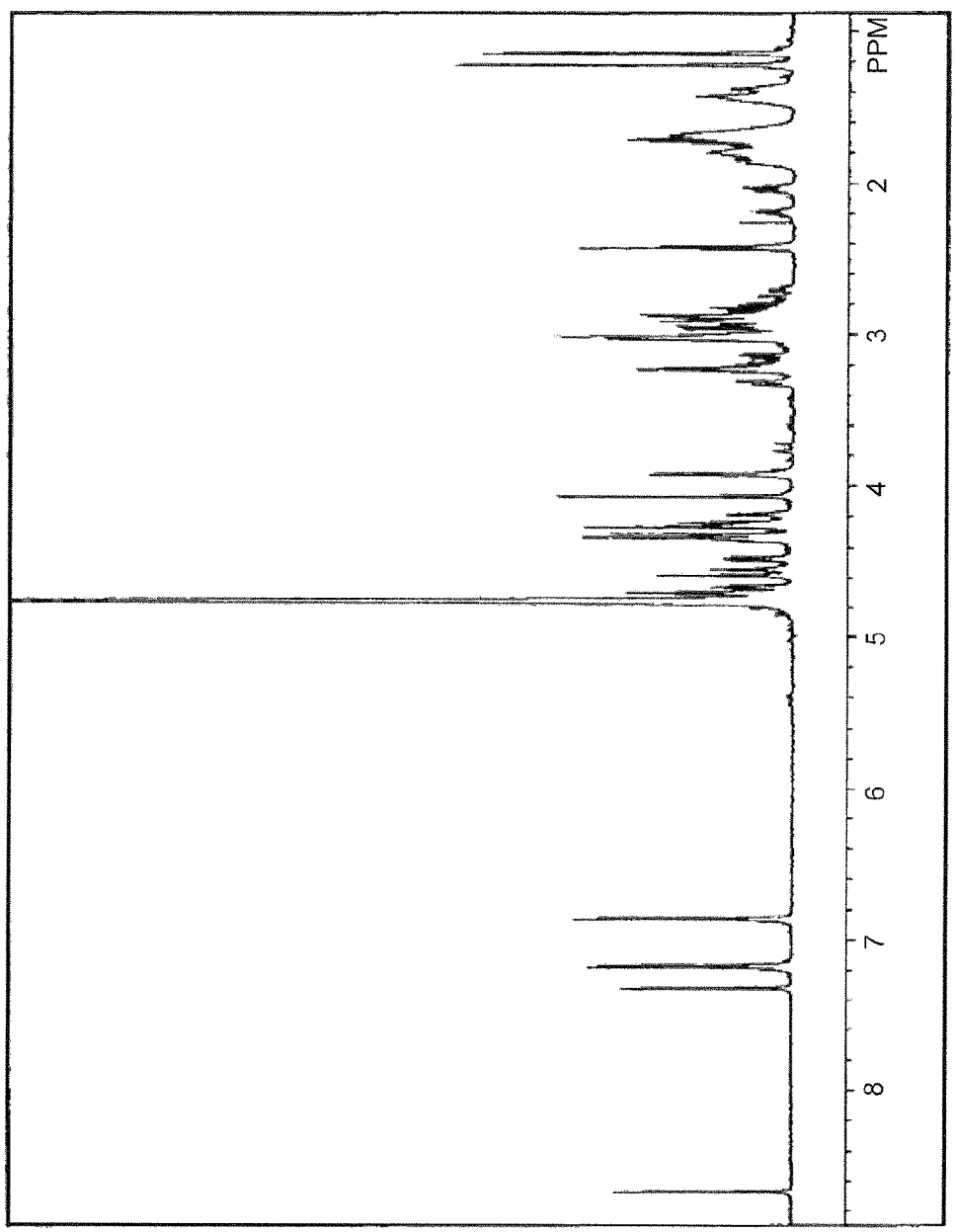
FIG. 4. $^1$H-NMR spectrum of the peptide SerSerGln-ThrAsnAspLysHisLysArg AspThrTyrGlySerGlySerGlyCys of the peptide-lipid construct designated DOPE-PEG$_6$-βAla-Mal-Milt(K)(M13) (4.5 mg/ml in D$_2$O, 600 MHz, 30° C., δ ppm).
Figure 5:
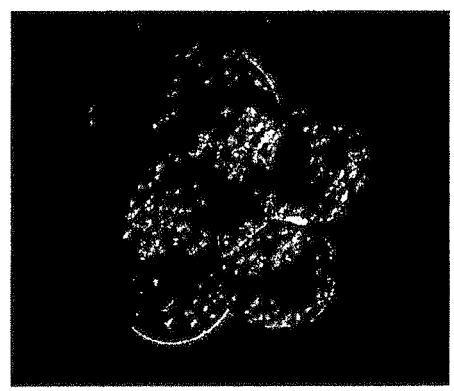
FIG. 5. Photomicrographs of zone free embryos modified to incorporate the M2 peptide-lipid construct by contacting the embryos with a dispersion of the construct at a concentration of 1 mg/mL for 2 hours. The upper photomicrograph is the DIC image. The lower photomicrograph is the fluorescent image showing 3.0+ fluorescence.
Figure 5:
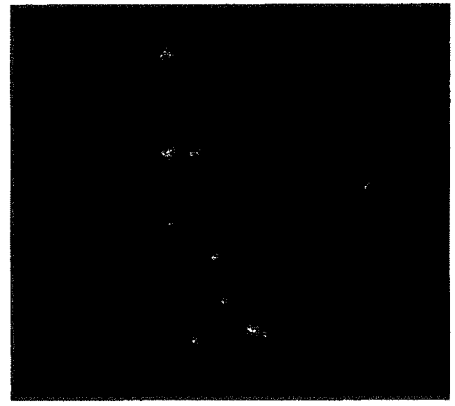

In general terms the invention provides peptide-lipid constructs of the structure $(L-S-)_iF(-S-L)_j$ where:

F is a peptide;

S is a spacer covalently linking F to L;

L is a lipid selected from the group consisting of diacyl- and dialkyl-glycerolipids, including glycerophospholipids;

i and j are independently 0 or 1;

and the use of these peptide-lipid constructs in diagnostic and therapeutic applications.

Where i is 0 and j is 1 the peptide-lipid constructs are of the structure:

F-S-L

Where i is 1 and j is 0 the peptide-lipid constructs are of the structure:

L-S-F

Where S is linked to F via the amino terminus of the peptide the construct is represented by the structure or substructure L-S-F.

Where S is linked to F via the carboxyl terminus of the peptide the construct is represented by the structure or substructure F-S-L.

Where S is linked to F via a sulphide bond formed via the sulfhydryl group of a Cys residue of the peptide the residue is identified with an underscore (Cys).

Where S is linked to F via a sulphide bond formed with one or more Cys residues of the peptide, the representation of the peptide-lipid construct by the structure L-S-F-S-L, L-S-F or F-S-L is not intended to imply the sulphide bond is formed exclusively with terminal Cys residues.

The use of the peptide-lipid constructs in diagnostic applications is illustrated with reference to the use of constructs including the substructure:

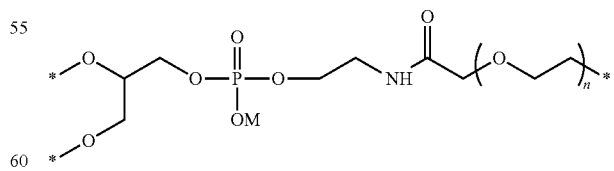

where M is a monovalent cation ($M^+$), n is 6 to 14, other than H, and the peptide is selected from the group of peptides consisting of peptides included in the List of Peptides provided on the following pages where z is an integer from 0 to 6.

| List of Peptides |
|---|
| <u>Cys</u>(Xaa)$_z$TrpThrProProArgAlaGlnIleThrGlyTyrLeuThrValGlyLeuThrArgArg |
| <u>Cys</u>(Xaa)$_z$TrpThrProProArgAlaGlnIleThrGlyTyrArgLeuThrValGlyLeuThrArgArg |
| <u>Cys</u>(Xaa)$_z$ValMetTyrAlaSerSerGly |
| ValMetTyrAlaSerSerGly(Xaa)$_z$<u>Cys</u> |
| AspTyrHisArgValMetTyrAlaSerSerGly(Xaa)$_z$<u>Cys</u> |
| ThrAsnGlyGluThrGlyGlnLeuValHisArgPhe(Xaa)$_z$<u>Cys</u> |
| ThrAsnGlyGluMetGlyGlnLeuValHisArgPhe(Xaa)$_z$<u>Cys</u> |
| AspThrTyrProAlaHisThrAlaAsnGluValSerGlu(Xaa)$_z$<u>Cys</u> |
| ThrTyrProAlaHisThrAlaAsnGluVal(Xaa)$_z$<u>Cys</u> |
| ProAlaHisThrAlaAsnGluVal(Xaa)$_z$<u>Cys</u> |
| TyrProAlaHisThrAlaAsnGlu(Xaa)$_z$<u>Cys</u> |
| ThrTyrProAlaHisThrAlaAsn(Xaa)$_z$<u>Cys</u> |
| ThrTyrProAlaHisThrAlaAsnGlu(Xaa)$_z$<u>Cys</u> |
| TyrProAlaHisThrAlaAsnGluVal(Xaa)$_z$<u>Cys</u> |
| ProAlaHisThrAlaAsnGluValSer(Xaa)$_z$<u>Cys</u> |
| AspThrTyrProAlaHisThrAlaAsnGlu(Xaa)$_z$<u>Cys</u> |
| TyrProAlaHisThrAlaAsnGluValSer(Xaa)$_z$<u>Cys</u> |
| SerGlnThrAsnAspLysHisLysArgAsp(Xaa)$_z$<u>Cys</u> |
| GlnThrAsnAspLysHisLysArgAspThrTyr(Xaa)$_z$<u>Cys</u> |
| GlnThrAsnAspLysHisLysArgAspThrTyrSerSerGlnThrAsnAspMetHisLysArgAspThrTyr(Xaa)$_z$<u>Cys</u> |
| GlnThrAsnAspMetHisLysArgAspThrTyr(Xaa)$_z$<u>Cys</u> |
| SerSerGlnThrAsnAspLysHisLysArg(Xaa)$_z$<u>Cys</u> |
| SerSerGlnThrAsnAspLysHisLysArgAspThrTyr(Xaa)$_z$<u>Cys</u> |
| SerSerGlnThrAsnAspMetHisLysArgAspThrTyr(Xaa)$_z$<u>Cys</u> |
| SerSerGlnThrAsnAspLysHisLysArgAspThrTyrSerSerGlnThrAsnAspMetHisLysArgAspThrTyr(Xaa)$_z$<u>Cys</u> |
| GlnThrAsnAspLysHisLysArgAspThr(Xaa)$_z$<u>Cys</u> |
| SerGlnThrAsnAspLysHisLysArgAspThr(Xaa)$_z$<u>Cys</u> |
| ThrAsnAspLysHisLysArgAspThrTyrPro(Xaa)$_z$<u>Cys</u> |
| GluGluThrGlyGluThrGlyGlnLeuVal(Xaa)$_z$<u>Cys</u> |
| GluGluGluThrGlyGluThrGlyGlnLeu(Xaa)$_z$<u>Cys</u> |
| GluThrGlyGluThrGlyGlnLeuValHis(Xaa)$_z$<u>Cys</u> |
| SerProProArgArgAlaArgValThr(Xaa)$_z$<u>Cys</u> |
| TyrArgTyrArgTyrThrProLysGluLysThrGlyProMetLysGlu(Xaa)$_z$<u>Cys</u> |
| TrpGlnProProArgAlaArgIle(Xaa)$_z$<u>Cys</u> |
| ThrIleThrGlyLeuGluProGlyThrGlu(Xaa)$_z$<u>Cys</u> |

The amino acid residues of peptides are identified according to Table 3 of Appendix 2 of Annex C of the *Administrative Instructions under the Patent Cooperation Treaty* dated 7 Feb. 2007 and in accordance with the convention:

```
H₂N-XaaXaaXaa . . . XaaXaaXaa-COOH
```

There is a need for inexpensive and low level sensitivity test systems for a range of diagnostic markers in donated blood, in transfusion recipients, or in antenatal patients (where the unborn child may be at risk of haemolytic disease), e.g. syphilis markers and markers of the MNS blood group system. A particular advantage provided by the invention is the opportunity to employ established blood typing platforms to detect a range of peptide antigen-antibody interactions. The capital costs associated with establishing a new diagnostic assay may therefore be avoided.

Some clinically significant blood group antigens are rare (or rare in some populations). For example mutations of the MNS blood group system resulting in Miltenberger antigens are rare in Europeans, but common in Asians. Being able to create antibody detection and identification panels requires that these antigens be present on the diagnostic screening cells. Obtaining ells suitable fort antibody screening/identification having rare antigens is therefore problematic. Being able to add to cells rare antigens prepared exogenously is therefore a major advantage.

According to the method of the invention epitope containing peptide sequences for a range of diagnostic markers, such as specific reacting antibodies, an be localized to the surface of red blood cells (RBCs). These modified RBCs may then be used on existing blood typing platforms to detect blood antobodies or pathologies.

Although the invention is illustrated with reference to the modification of red blood cells and embryos the outer surface of other cells and multi-cellular structures is contemplated. However, red blood cells are preferred for use in diagnostic assays because of the facility with which these modified cells could be used in blood typing laboratories.

The level of peptide-lipid construct incorporated into the cell membrane of red blood cells is controlled by the concentration of the construct in the dispersion contacted with the suspension. The presence of diagnostic markers may then be assessed by agglutination whether direct (induced by centrifugation of cells) or indirect (induced by adding an antibody directed against the immunoglobulins of the subject). Other methods of assessment may be employed including, for example, rosetting (Indiveri et al 1979) and enzyme linked immunosorbant assays (ELISA).

In contrast with the preparation of constructs where the function (F) is a carbohydrate, the preparation of constructs where F is a peptide presents a combination of technical difficulties.

Firstly, it is desirable for the peptide (F) ligated to the L-S or S-L moiety to be dispersible in the solvents used for the ligation chemistry. Overcoming this difficulty may require the selection of a proximal terminal sequence (PTS) to promote solubility without modifying the desired biological properties of the construct.

Secondly, it is r for the construct (L-S-F-S-L, L-S-F or F-S-L) to be dispersible in water, or at least a biocompatible medium such as buffered saline, according to the requirements of the proposed application (i.e. it is desirable for the construct to be "water soluble" as defined herein). Overcoming this difficulty requires the selection of a spacer (S) to promote solubility of the construct.

Thirdly, where the proposed application is the modification of cells such as red blood cells (RBCs) for use in diagnostic applications, including use as quality controls in blood group typing or detection of diagnostic antibodies present in patient serum, it is required for the construct to be dispersible without participating in antigen-antibody cross reactivity not specific to the diagnostic marker. Satisfying this requirement requires the identification of suitable structural motifs for the spacer (S) and proximal terminal sequence (PTS) when the latter is present, or the development of sample preparation procedures that neutralize or at least substantially mitigate the undesired cross reactivity and likelihood of false positives.

It should also be noted that where the application is for use in the modification of the surface of cells or multi-cellular structures (e.g. an embryo) with a view to promoting the association of the modified cell or modified multi-cellular structure with a target surface (e.g. the endometrium) exposing the cell or multi-cellular structure to solvents is incompatible with maintaining the cells or multicellular structures in a viable state.

The ability to localise peptides to the surface of cells or multi-cellular structures via a residue proximal to either the N- or C-terminus of the peptide may also allow the naturally occurring configuration of the peptide sequence relative to the cell surface to be approximated. The presentation of the peptide sequence in the tertiary (or quaternary) structure of the parent polypeptide (or protein) may therefore be mimicked.

Although not demonstrated here it is contemplated that peptides may be localised to the surface of cells via multiple residues. For example, where both a residue proximal to the amino terminus and a residue proximal to the carboxyl terminus are used to localize the peptide, a "looped" configuration of the peptide may be promoted at the surface.

The use of polyethylene glycol (PEG) as a spacer to promote solubility is known. However, polymers of PEG may interfere with the expression and function of the peptide at the surface. In the peptide-lipid constructs of the invention an oligomer of ethylene glycol (6 to 14 mer) is selected as a component ($S_1$) of the spacer (S) linking the lipid (L) and peptide (F).

Oligomers of ethylene glycol impart less solubility to peptide-lipid constructs of the structure L-S-F than polymers of PEG. The difficulty referred to above therefore arises when it is desired to obtain peptide-lipid constructs that are dispersible in biocompatible solvents and can be used in methods of effecting qualitative and quantitative changes in the levels of peptide expressed at the surface of cells and multi-cellular structures.

The properties of the peptide-lipid constructs must be such that they can be readily dispersed in biologically compatible media in the absence of solvents or detergents, but incorporate into the lipid bilayer of a membrane when a solution of the construct is contacted with a suspension of cells or multi-cellular structures.

Peptide-lipid constructs with these potentially conflicting properties are prepared by adopting the combination of structural motifs described here. The preparation of the peptide-lipid constructs where S is linked to F via a sulphide bond formed with a terminal Cys residue of the peptide at the carboxy-terminus of the peptide is preferred as the peptide is less prone to oxidation.

Adopting the combinations of structural motifs in accordance, with the description provided here a range of peptides may be prepared as peptide-lipid constructs for use in methods of effecting qualitative and quantitative changes in the levels of peptide expressed at the surface of cells and multi-cellular structures.

It will be understood that for a non-specific interaction, such as the interaction between diacyl- or dialkyl-glycerolipids or glycerophospholipids and a membrane, structural and stereo-isomers of naturally occurring lipids can be functionally equivalent. For example, it is contemplated that diacylglycerol 2-phosphate could be substituted for phosphatidate (diacylglycerol 3-phosphate). Furthermore it is contemplated that the absolute configuration of phosphatidate can be either R or S.

Preparation of DOPE-PEG$_6$-NH$_2$ (7)

DOPE-PEG$_G$-NH$_2$ (L-S$_1$—NH$_2$) (7, 800 mg) was prepared by the method of SCHEME 1. To a stirred solution of DOPE (5) (36 mg, 0.0484 mmol) in dry CHCl$_3$ (3 ml) a solution of Fmoc-PEG-NOS (4) (237 mg, 0.0697 mmol (containing about 80% of active N-oxysuccinimide ester)) in dry CHCl$_3$ (1 ml) and Et$_3$NH (30 ml) was added.

The solution was stirred for 15 h at 20° C., then Et$_3$NH (3 ml) was added, and the mixture was maintained for at 8 h at 20° C. The solution was then diluted with toluene (10 ml), evaporated under reduced pressure (10 to 15 torr) and dried under vacuum.

The crude residue was dissolved in H$_2$O/MeOH/AcOH mixture (10:5:1 (v/v/v), 3 ml) and the solution was slowly applied to a reverse phase C$_{16}$ column (15 ml, water). Salts, N-hydroxysuccinimide and H$_2$N-PEG-DOPE (7) were eluted from the column with MeOH/H$_2$O 1:2 (v/v) (30 ml), 1:1 (v/v) (15 ml) and 2:1 (v/v) (15 ml). Target H$_2$N-PEG-DOPE (7) was eluted from the column with MeOH (30 ml) and then with MeOH to MeOH/CHCl$_3$ mixtures (4:1 (v/v), 3:1 (v/v), 2:1 (v/v) and 1:1 (v/v); 30 ml each). Fractions containing H$_2$N-PEG-DOPE (7) were combined, evaporated under reduced pressure (10 to 15 torr) and dried under vacuum.

The residue obtained as a thin film on the flask walls was extracted twice with hexane (2×5 ml) and dried under vacuum to yield 143 mg of H$_2$N-PEG-DOPE (7) (78% on DOPE) as a white solid. TLC: R$_f$=0.62 (ethanol/water/pyridine/AcOH; 3:1:1:1 (v/v/v/v)).

$^1$H-NMR (500 MHz, CO$_3$OD, 30° C.): δ=5.541 (m, 4H; 2-C$\underline{H}$=C$\underline{H}$—), 5.416 (m, 1H; OCH$_2$C$\underline{H}$CH$_2$O), 4.624 (dd, J=12 Hz, J=3.2 Hz, 1H; CO—OC$\underline{H}$CHCH$_2$), 4.373 (dd, J=12 Hz, J=6.6 Hz, 1H; CO—OC$\underline{H}$CHCH$_2$), 4.195 (t, J=5.6 Hz, 2H; POC$\underline{H}_2$CH$_2$N), 4.117 (m, 2H; POC$\underline{H}$CHCH$_2$), 3.968 (m, 4H; OC$\underline{H}_2$CH$_2$O, OC$\underline{H}_2$CH$_2$N), 3.932 (t, J=6.2 Hz, 2H; OC$\underline{H}_2$CH$_2$CO), 3.827 (m, 272H; (—OC$\underline{H}_2$CH$_2$)$_n$, n=68), 3.683 (m, 2H; OC$\underline{H}_2$CH$_2$O), 3.622 (t, J=5.6 Hz, 25; OCH$_2$C$\underline{H}_2$N), 3.397 (t, J=5.0 Hz, 2H; OCH$_2$CH$_2$N), 2.678 (t, J=6.2 Hz, 2H; OCH$_2$C$\underline{H}_2$CO), 2.519 (m, 4H; 2 CH$_2$CO), 2.228 (m, 85; 2 CH$_2$CH=CHCH$_2$), 1.801 (m, 45; 2 CH$_2$CH$_2$CO), 1.508 (m, 40H; —CH$_2$—), 1.096 (~t, 6H; 2 CH$_3$) ppm.

Preparation of Peptide-Lipid Constructs

Maleimido-derivatives of DOPE-PEG$_6$-NH$_2$ were used for the preparation of peptide-lipid constructs (L-S-F) by the method of SCHEME 2 via the maleimide-thiol Michael addition reaction.

Synthesis via the maleimido-derivatives of DOPE-PEG$_5$-NH$_2$ has particular advantages over synthesis via iodoacetate derivatives as difficulties and low yields as a consequence of oxidation of the sulfhydryl residues of the peptide and subsequent dimer formation. Reducing agents (e.g. tertiary phosphines) may be used during conjugation.

Maleimido-derivatives were synthesized with 65 to 70% yields starting from N-oxysuccinimid esters of maleimidobutyric and maleimidopropionic acids (8a, 8b). An unexpected complication arose due to the presence of excess Bu$_3$P which appeared to be highly reactive towards the maleimide function. Phosphine was therefore used only in sub-equivalent amounts (0:1 to 0.2 equivalents).

SCHEME 1

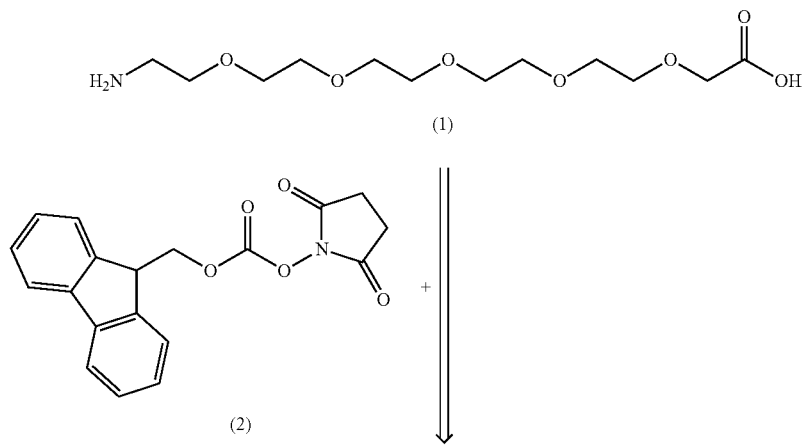

-continued
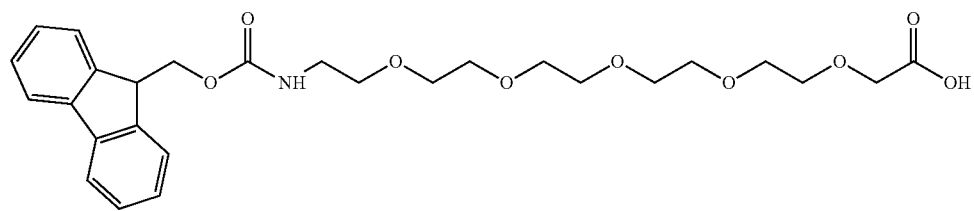
(3)
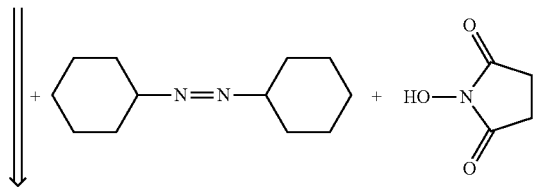
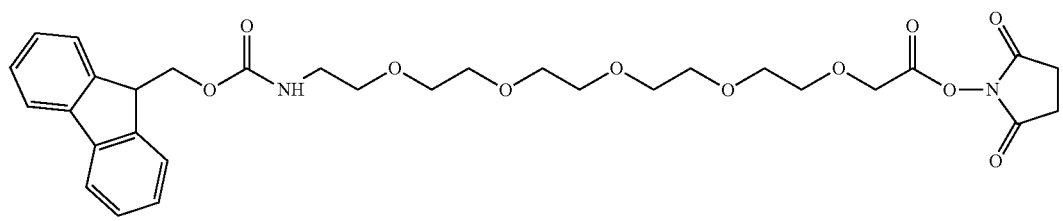
(4)
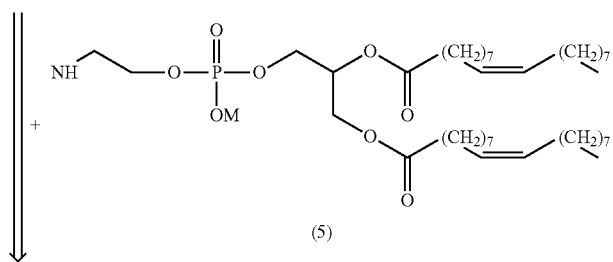
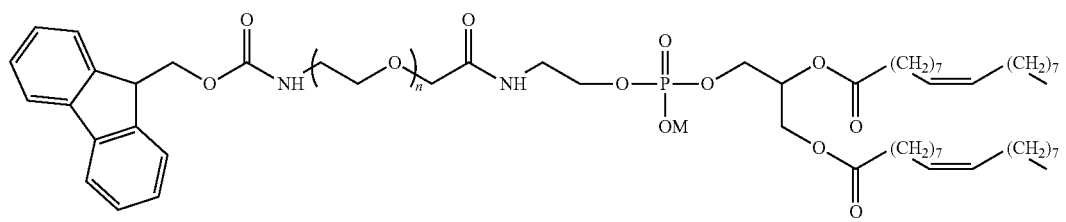
(6)
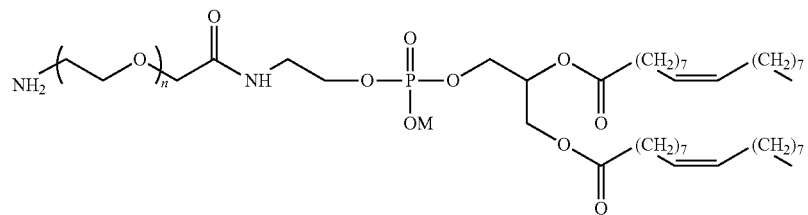
(7)

Trifluoroethanol used as a co-solvent in the preparation of 10bC where the peptide was GlnThrAsnAspMetHisLysArgAspThrTyr-GlySerGlySerGlyCys appeared to be highly efficient for solubilization of both reactants. However, the solvent also caused unwanted acidification of the reaction medium which may inhibit the Michael reaction. The isolated yield of 10bC in this experiment was ~25%. Preparation of 10aC where the peptide was GlnThrAsnAspMetHisLysArgAspThrTyrGlySerGlySerGly-Cys (DOPE-$PEG_6$-βAla-Mal-3MUTM (M3)) carried out using DMSO as co-solvent was more successful and provided a 43% yield.

The same solvent strategy in the preparation of 10bC where the peptide was GlnThrAsnAspLysHisLysArgAspThrTyrSerSerGlnThrAsn-AspMethisLysArgAspThrTyrAlaAlaAlaAlaCys (DOPE-$PEG_6$-βAla-Mal-PTS-Milt(K,M)) failed because the peptide supplied appeared to be very acidic and caused solubilization problems. The yield of 10bC in this experiment was only 23% and about half of the peptide was recovered.

Molecular weights for the peptide lipid constructs were determined to be:

DOPE-$PEG_6$-βAla-Mal-Milt(M)-3029.48

DOPE-$PEG_6$-βAla-Mal-Milt(K,M)-4591.12

As expected for peptides bearing the glutamine residue at the N-terminus, all preparations contain variable amounts of related pyroglytamyl derivatives, M-17 in MS, due to loss of $NH_3$. The formation of related pyroglytamyl derivatives was mitigated in peptides with N-terminal Ser residues.

The use of the peptide-lipid constructs in methods for effecting qualitative and quantitative changes in the levels of peptide expressed at the surface of cells and multi-cellular structures is illustrated with reference to the serodiagnosis.

Modification of Red Blood Cells with Peptide-Lipid Constructs (General Method)

Red blood cells are modified by mixing 1 part by volume of washed packed red blood cells with 1 part by volume of peptide-lipid construct dispersed at a concentration of 10 to 1000 μg/ml in cell media (Celpresol™).

The suspensions are either:
1. incubated for 2 hours at 37° C. before being washed and suspended in a cell medium for serological analysis at a concentration of 0.8 to 3% (Method 1); or
2. incubated for 3 to 4 hours at room temperature (circa 25° C.) followed by 18, hours at 4° C. before being washed and suspended in a cell medium for serological analysis at a concentration of 0.8 to 3% (Method 2).

Modification of Red Blood Cells with DOPE-$PEG_6$-βAla-Mal-Milt (K) (M00)

4.7 mg of the lipid-peptide construct DOPE-$PEG_6$-βAla-Mal-Milt(K) (M00) was reconstituted in 0.47 ml of Celpresol™ by sonicating for 10 min and allowing to stand for 1 hour to provide a clear 10 mg/ml stock solution.

SCHEME 2

(7)

(8a w = 1; 8b w = 2)

(9a w = 1; 9b w = 2)

-continued

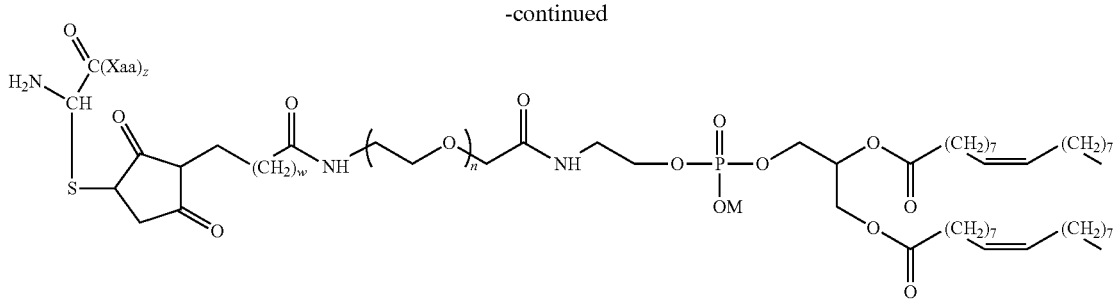

(10aN w = 1; 10bN w = 2)

or

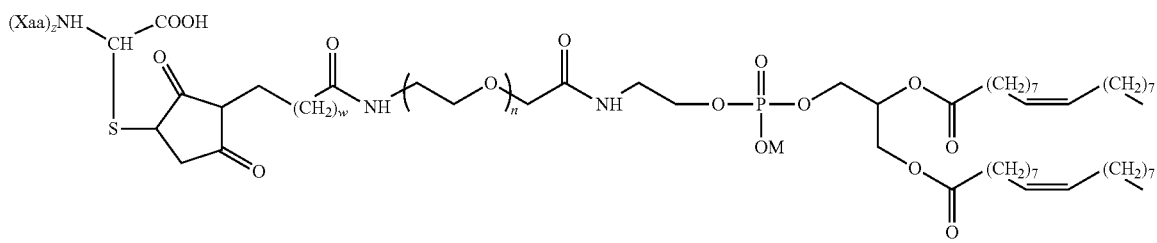

(10aC w = 1; 10bC w = 2)

The stock solution was diluted two-fold to provide a solution of 5 mg/ml and a dilution series then prepared for the peptide-lipid construct at the following concentrations:

1 mg/ml (1:5 dilution in Celpresol™)
0.5 mg/ml (1:10 dilution in Celpresol™)
0.25 mg/ml (1:20 dilution in Celpresol™)

200 μl of Miltenberger negative red blood cells (Milt⁻ RBCs) were washed two times with PBS and one time with Celpresol™. 40 μl of a washed packed volume of Milt⁻ RBCs were mixed with 40 μl of a dilution of the peptide-lipid construct and incubated for 2 hours at 37° C.

The modified RBCs were then washed with Celpresol™ and stored in Celpresol™ until used in tube serology testing (3 days and 24 days).

Tube Serology Testing of Modified Red Blood Cells

Serological reactions are graded or scored by either of two established systems (0 or '−'=no agglutination, 1+ or 3=very weak agglutination, 2+ or 5=weak agglutination, 3+ or 8=moderate strong agglutination, 4+ or 10/12=strong agglutination)

Serological platforms used are Tube (addition of reagents and reactants into plastic or glass serology tubes and after appropriate incubations, washing and centrifugation observing reactions macroscopically by eye and a 10× magnification eyepiece and scoring) and BioVue™ (addition of reactants into cassettes containing beads (including some reactants) and after appropriate incubations and centrifugation observing the reaction patterns trapped within the Gel matrix). BioVue is the serological column agglutination platform of Ortho-Clinical Diagnostics.

Serum samples were available from 47 blood donors of negative antibody screen status. These samples were designated "negative samples", but not determined not to have anti-Miltenberger antibodies).

Three serum samples known to have Miltenberger related antibodies T217, T6025, T5896. These samples were designated "positive samples", but not determined to have anti-antibodies against the peptide of the peptide of the construct designated DOPE-PEG₆-βAla-Mal-Milt(K) (M00).

A suspension of 3% modified RBCs was prepared in PBS and 30 μl of the suspension mixed with 30 μl serum sample. The mixtures were then incubated for 45 min at 37° C. Following incubation the RBCs were centrifuged for 10 s in an Immufuge™ (setting: "high") and observed for agglutination before being washed 3 times with PBS.

After washing one drop of Epiclone™ anti-human globulin (AHG) was added and the tubes then centrifuged for 10 s in an Immufuge™ (setting: "high"). Tubes were then read and serology scores recorded.

TABLE 1

Summary of reactivity of samples of serum from 47 blood donors not expected to have anti-Miltenberger activity ("negative samples").

| Age of modified RBCs (days) | Serum | Concentration of DOPE-PEG$_6$-βAla-Mal-Milt(K)(M00) (mg/ml) | | | | | |
|---|---|---|---|---|---|---|---|
| | | 1.0 (n = 47) | | 0.5 (n = 21) | | 0.25 (n = 21) | |
| | | AHG+ | AHG− | AHG+ | AHG− | AHG+ | AHG− |
| 3 | Negative samples | 1 | 46 | 0 | 21 | 0 | 21 |

AHG+ means sample reacted by the anti-human globulin test.
AHG− means sample is unreactive.
RBCs were modified with the peptide-lipid construct designated DOPE-PEG$_6$-βAla-Mal-Milt(K) at the concentrations indicated.
Sera were tested against modified RBCs following 3 days storage.

TABLE 2

Results by tube serology of 3 serums known to contain antibodies against antigens of the Miltenberger complex.

| Age of modified RBCs (days) | Serum | Concentration of DOPE-PEG$_6$-βAla-Mal-Milt (K) (M00) (mg/ml) | | |
|---|---|---|---|---|
| | | 1.0 | 0.5 | 0.25 |
| 3 | T217 | 2+ | 1+ | — |
| 3 | T6025 | 4+ | 4+ | 4+ |
| 3 | T5896 | — | — | — |
| 24 | T217 | — | — | n.t. |
| 24 | T6025 | 2+ | 2+ | n.t. |
| 24 | T5896 | — | — | n.t. |

Score results show sample reactivity by the anti-human globulin test, 1+ = weak, 2+ = medium, 3+ = medium/strong, 4+ = strong, — means sample is unreactive. RBCs were modified with the peptide-lipid construct, at the concentrations indicated. Sera were tested against modified RBCs following 3 days and 24 days storage.
(n.t.—not tested).

TABLE 3

Results by Diamed column serology of 3 serums known to contain antibodies against the Miltenberger complex.

| Age of modified RBCs (days) | Serum | Concentration of DOPE-PEG$_6$-βAla-Mal-Milt (K) (M00) (mg/ml) | | |
|---|---|---|---|---|
| | | 1.0 | 0.5 | 0.25 |
| 3 | T217 | — | — | 1+ |
| 3 | T6025 | 1+ | 2+ | 1+ |
| 3 | T5896 | — | — | — |
| 24 | T217 | — | — | — |
| 24 | T6025 | 2+ | 2+ | 1+ |
| 24 | T5896 | — | — | — |

Score results show sample reactivity by the anti-human globulin test, 1+ = weak, 2+ = medium, 3+ = medium/strong, 4+ = strong, — means sample is unreactive. RBCs were modified with the peptide-lipid construct at the concentrations indicated. Sera were tested against modified RBCs following 3 days and 24 days storage.

Peptide Inhibition

A 5 mg/ml stock solution of the peptide GlnThrAsnAspLysHisLys-ArgAspThrTyrCys dissolved in Celpresol™ was prepared. A 4 µl (20 µg peptide) volume of the stock solution was added to a 30 µl volume of each serum sample (Test). A 4 µl volume of Celpresol™ was added to 30 µl of each serum sample (Control). Serum samples (Test and Control) were then incubated at room temperature (RT) for 10 min.

A 30 µl volume of a 5% suspension of the modified RBCs was added to each sample and incubated at 37° C. for 45 min. The incubated RBCs were then washed 3 times with PBS in an Immufuge™. One drop of Epiclone™ anti-human globulin (AHG) reagent was then added to each sample and the tubes centrifuged for 10 s in an Immufuge™ (setting: "high"). Tubes were read and serology scores recorded.

TABLE 4

Results by tube serology of 3 serums known to contain antibodies against the Miltenberger complex and inhibited with peptide.

| Peptide | Serum | Concentration of DOPE-PEG$_6$-βAla-Mal-Milt (K) (M00) (mg/ml) | |
|---|---|---|---|
| | | 1.0 | 0.5 |
| CONTROL | T217 | 3+ | 2+ |
| | T6025 | 4+ | 4+ |
| | T5B96 | — | — |
| TEST | T217 | — | — |
| | T6025 | — | — |
| | T5896 | — | — |

Recorded scores show sample reactivity by the anti-human globulin test, 1+ = weak, 2+ = medium, 3+ = medium/strong, 4+ = strong, — means sample is unreactive. RBCs were modified with the peptide-lipid construct at the concentrations indicated.

TABLE 5

Identification of polyclonal sera and monoclonal antibodies employed as reagents.

| Reagent ID | Type | EIA/Miltenberger Specificity |
|---|---|---|
| 2 | T217 | Human group AB serum | Reactive with MUT-T peptides by EIA |
| 3 | T165 | Human group O serum | Reactive with MUR peptides by EIA |
| 4 | T7202 | Human group B serum | Reactive with MUT-M peptides by EIA |
| 6 | T6025 | Human group A serum | Reactive with MUT-T peptides by EIA |
| 7 | T8445 | Human group O serum | Uncertain |
| 8 | T5896 | Human group O serum | Uncertain |
| 9 | MIII | Monoclonal antibody | Reactive with Mi III red cells |
| 10 | Mia | Monoclonal antibody | Reactive with Mi III red cells |
| 11 | Mur | Monoclonal antibody | Reactive with Mur positive red cells |

TABLE 5-continued

| Identification of polyclonal sera and monoclonal antibodies employed as reagents. | | | |
|---|---|---|---|
| Reagent | ID | Type | EIA/Miltenberger Specificity |
| 12 | Gam | IgG monoclonal antibody | Reactive with Mi III red cells |
| 13 | BoxH | Human serum | Uncertain |
| 14 | TAP1 | Human group O serum | Presumed MUT-R specificity |
| 15 | TAP2 | Human serum | Presumed MUR specificity |

TABLE 6

Identification of naturally occurring Miltenberger antigen positive ($Milt^+$) human red cells as determined in BioVue AHG cards. The specificity of C.BR is uncertain.

| | | Polyclonal sera | | | | | | | | Monoclonal antibodies | | | |
|---|---|---|---|---|---|---|---|---|---|---|---|---|---|
| Cell ID | Antigen | 2 T217 | 3 T165 | 4 T7202 | 6 T6025 | 7 T8445 | 8 T5896 | 14 TAP1 | 15 TAP2 | 9 MIII | 10 Mia | 11 Mur | 12 Gam |
| 9422184 | Vw | 8 | 5 | 3 | 0 | 8 | 0 | 5 | 0 | 0 | 10 | 0 | 12 |
| 11297161 | MiIII | 12 | 10 | 12 | 12 | 10 | 10 | 10 | | 10 | 10 | 12 | 12 |
| 4131850 | MiIV | 12 | | | 12 | | | | 10 | 0 | 10 | 12 | 12 |
| 1523 | MiVI | 12 | | | 12 | | | | 8 | 0 | 10 | 12 | 10 |
| T1569 | MiVII | 0 | 0 | 0 | 0 | 10 | 0 | 0 | | 0 | 0 | 0 | 0 |
| C.BR | Mi?X | 12 | 10 | 12 | 12 | 8 | 12 | 12 | 8 | 0 | 10 | 10 | 10 |

TABLE 7

Identification of peptide-lipid constructs.

| Designation | | Peptide sequence | | | | | | | | | | | | | |
|---|---|---|---|---|---|---|---|---|---|---|---|---|---|---|---|
| M | Antigen | 1 | 2 | 3 | 4 | 5 | 6 | 7 | 8 | 9 | 10 | 11 | 12 | 13 | Terminal sequence | $S_1$ |
| 1 | MUTK | | | Gln | Thr | Asn | Asp | Lys | His | Lys | Arg | Asp | Thr | Tyr | AlaAlaAlaAlaAla* | $PEG_6$ |
| 2 | MUTK | | | Gln | Thr | Asn | Asp | Lys | His | Lys | Arg | Asp | Thr | Tyr | GlySerGlySerGlyCys | $PEG_6$ |
| 3 | MUTM | | | Gln | Thr | Asn | Asp | Met | His | Lys | Arg | Asp | Thr | Tyr | GlySerGlySerGlyCys | $PEG_6$ |
| 13 | MUTK | Ser | Ser | Gln | Thr | Asn | Asp | Lys | His | Lys | Arg | Asp | Thr | Tyr | Cys | $PEG_6$ |
| 16 | Mur | | Thr | Tyr | Pro | Ala | His | Thr | Ala | Asn | Glu | Val | | | Cys | PEG |
| 18 | Mur | | | | Pro | Ala | His | Thr | Ala | Asn | Glu | Val | | | Cys | PEG |
| 21 | MUTK | | Ser | Gln | Thr | Asn | Asp | Lys | His | Lys | Arg | Asp | | | Cys | PEG |
| 23 | Hil | | Glu | Glu | Thr | Gly | Glu | Thr | Gly | Gln | Leu | Val | | | Cys | PEG |

Cys denotes the cysteine residue via the sulfhydryl residue of which the spacer (S) is covalently linked to the peptide or PTS-peptide (F).
*Where Cys is absent the spacer (S) is covalently linked to the peptide (F) via the terminal amino residue.
All peptide-lipid constructs (F-S-L or L-S-F) were prepared as the DOPE (L) variant.

TABLE 8

Analysis of sorted data for cells modified to incorporate MUT peptide constructs and reactivity against the Miltenberger Antibody Positive Panel.

| Identity of constructs used in modification of RBCs (see Table 7) | | Identity of polyclonal sera and monoclonal antibodies (see Table 5) | | | | | | | | | | | | |
|---|---|---|---|---|---|---|---|---|---|---|---|---|---|---|
| | | 4 | 8 | 2 | 6 | 3 | 14 | 7 | 9 | 10 | 11 | 12 | 13 | 15 |
| M | μg/ml | T7202 | T5896 | T217 | T6025 | T165 | TAP1 | T8445 | MIII | Mia | Mur | Gam | BoxH | TAP2 |
| 1 | 500 | 5 | 0 | 3 | 8 | 0 | nt | 0 | 0 | 5 | 0 | 8 | nt | nt |
| 2 | 500 | 8 | 8 | 8 | 8 | 5 | nt | 0 | 0 | 5 | 0 | 8 | nt | nt |
| 3 | 1000 | 8 | 10 | 0 | | 5 | nt | 0 | 0 | 0 | 0 | nt | 5 | nt |
| 13 | 250 | 8 | 3 | 8 | 8 | 0 | nt | 0 | 0 | 0 | 0 | 0 | 8 | nt |
| 21 | 200 | 0 | 0 | 0 | 8 | 8 | nt | 0 | 0 | 0 | 0 | 3 | nt | 5 |

'nt' denotes not tested.

TABLE 9

Analysis of sorted data for cells modified to incorporate MUR peptide constructs and reactivity against the Miltenberger Antibody Positive Panel.

| Identity of constructs used in modification of RBCs (see Table 7) | | Identity of polyclonal sera and monoclonal antibodies (see Table 5) | | | | | | | | | | |
|---|---|---|---|---|---|---|---|---|---|---|---|---|
| | | 3 | 6 | 7 | 4 | 8 | 2 | 15 | 9 | 10 | 11 | 12 | 13 |
| M | ug/ml | T165 | T6025 | T8445 | T7202 | T5896 | T217 | TAP2 | MIII | Mia | Mur | Gam | BoxH |
| 16 | 100 | 10 | 5 | 12 | 5 | 0 | 0 | nt | 0 | 0 | 0 | 0 | 0 |
| 18 | 100 | 10 | 10 | 8 | 0 | 0 | 0 | nt | 0 | 0 | 0 | 0 | nt |

'nt' denotes not tested.

The majority of polyclonal sera demonstrated cross reactivity with one or more modified red blood cell populations (Tables 8 and 9).

Where false positives were observed these could be substantially eliminated by pre-treatment of the sample of serum with the peptide of the peptide-lipid constructs (Table 10 and 11).

TABLE 10

Sera reactive with RBCs modified to incorporate the M1 peptide-lipid construct or M2 peptide-lipid construct constructs by contacting the cells with a 500 µg/ml dispersion of the construct (Method 1) were "neutralised" with the peptide QTNDKHKRDTY and retested against the modified cells. Sera were neutralized by adding 10 µL of 1 mg/ml solution of peptide to a 50 µL volume of sera and incubating for 30 minutes at 37° C. Testing was performed using BioVue ™ cards.

| | M1 modified cells | | | M2 cells vs serum | | |
|---|---|---|---|---|---|---|
| Identity of sera | #4 | #5 | #6 | #2 | #6 | #8 |
| Serum alone | 5 | 5 | 10 | 8 | 8 | 8 |
| Serum + peptide | 0 | 0 | 0 | 0 | 2 | 0 |

TABLE 11

Sera reactive with ABCs modified to incorporate the M13 peptide-lipid construct by contacting the cells with a 500 µg/ml dispersion of the construct (Method 1) were "neutralised" with the peptide SSQTNDKHKRDTY and retested against the modified cells. Sera were neutralized by adding 10 µL of 1 mg/ml solution of peptide to a 50 µL volume of sera and incubating for 30 minutes at 37° C. Testing was performed using BioVue ® cards.

| | M13 modified cells | | | |
|---|---|---|---|---|
| Identity of sera | #3 | #42 | #37 | #34 |
| Serum alone | 8 | 8 | 8 | 8 |
| Serum + peptide | 0 | 0 | 0 | 0 |

Modification of Embryos with the Peptide-Lipid Construct Designated DOPE-PEG6-βAla-Mal-PTS-Milt(K) (M2)

The zona pellucida of day 3.5 embryos prepared as microdrops were removed by incubation in 0.5% pronase solution for circa minutes at 37° C. The zona pellucida removed embryos were transferred to microdrops containing media alone and contacted with a dispersion of the peptide-lipid construct designated DOPE-PEG6-βAla-Mal-PTS-Milt(K) (M2) at a concentration of 1 mg/ml for 2 hours. The dispersion of the peptide-lipid construct contained azide as an anti-microbial agent.

The incubated embryos were washed four times in handling media and transferred to microdrops containing the Gam monoclonal antibody (see Table 8) and incubated at 37° C. for 40 min. The embryos were then washed four times in handling media and transferred to microdrops containing secondary antibody (FITC anti-mouse) at a 1:50 dilution.

The microdrops were incubated at room temperature in the dark for 30 minutes before being washed four times in handling media, placed on microscope slides, and overlaid with mineral oil. The embryos were visualized using an Olympus™ BX51 fluorescent microscope at 200× magnification with WIB filter 550 nm emission wavelength. The scale used for grading fluorescence was 0 to 4+, where 0 is no fluorescence and 4+ is very bright fluorescence. The mean fluorescence of the modified embryos was 2+ versus zero for unmodified embryos. The grading of fluorescence is recorded in Table 12.

TABLE 12

Fluorescence of embryos modified by contacting with the peptide-lipid construct designated DOPE-PEG6-βAla-Mal-PTS-Milt (K) (M2) (10 embryos per group; scale is 0 to 4+).

| Mean Fluorescence* | |
|---|---|
| M2 FSL-peptide | Media alone |
| 2.0+ | 0 |

A mean fluorescence of 2+ was observed for the zona pellucida removed embryos modified to incorporate the peptide-lipid construct designated DOPE-PEG6-βAla-Mal-PTS-Milt(K) (M2). No fluorescence was observed for control embryos. The de-compaction of treated embryos was attributed to the presence of azide in the dispersion of the peptide-lipid construct.

Although the invention has been described by way of exemplifying embodiments it should be appreciated that variations and modifications may be made without departing from the scope of the invention. Furthermore where known equivalents exist to specific features, such equivalents are incorporated as if specifically referred to in this specification.

REFERENCE

Blume et al (1993) *Specific targeting with poly(thylene glycol)-modified liposomes coupling of homing devices to the ends of the polymeric chains combines effective target binding with long circulation times* Biochimica et Biophysics Acta, 1149: 180-184

Chung et al (2004) *Casual Cell Surface Remodelling Using Biocompatible Lipid-poly(ethylene glycol)(n): Development of Stealth Cells and Monitoring of Cell Membrane*

Behaviour in Serum-supplemented Conditions J Biomed. Mater. Res, Part A, 70A/2:179-185

Haselgrüler et al (1995) *Sythesis and Applications of a New Poly(ethylene glycol) Derivative for the Crosslinking of Amines with Thiols* Bioconjugate Chem, 6: 242-248

Hashimoto et al (1986) *Iodacetylated and biotinylated liposomes: Effect of spacer length on sulfhydryl ligand binding and avidin precipitability* Biochim Biophys Acta, 856: 556-565, Ishida et al (2001) *Liposomes Bearing Polytheneglycol-Coupled Transferrin with Intracellular Targeting Property to the Solid Tumors* In Vivo Pharmaceutical Research, 18 (7): 1042-1048

Kato et al (2004) *Rapid Proprotein anchoring into the membranes of mammalian cells using oelyl chain and polyethylene glycol derivatives*

Kinsky et al (1983) *An alternative procedure for the preparation of immunogenic liposomal model membranes* J Immunol Method, 65: 295-306

Kung and Redemann (1986) *Synthesis of carboxyacyl derivatives of phosphatidylethanolamine and use as an efficient method for conjugation of protein to liposomes* Biochim Biophys Acta, 862: 435-439

Legler et al (2005) *Differential insertion of GPI-anchored GFPs into lipid rafts of live cells* FASEB J. 19, 73-75

Mannino et al (1993) *Liposomes as adjuvants for peptides: Preparation and use of immunogenic peptide-phospholipid complexes* Liposome Technology: 167-184

Martin et al (1990) Liposomes a Practical Approach, 163-182

Martin and Papahadjopoulos (1982) Irreversible coupling of immunoglobulin fragments to preformed vesicles. An improved method for liposome targeting. J Biol Chem, 257: 286-288

Massaguer et al (2001) Synthesis of RGD Containing Peptides. Comparative Study of their Incorporation to the Surface of 5-Fluoruridine Loaded Liposomes. Journal of Liposome Research, 11(I):103-113

McHugh et al (1995) Construction, purification, and functional incorporation on tumor cells of glycolipid-anchored human B7-1 (CD80) Proc. Natl. Acad. Sci. U.S.A. 92, 8059-8063

Medof et al (1996) *Cell surface engineering with GPI-anchored proteins* FASEB J. 10, 574-586

Morandat et al (2002) *Cholesterol dependent insertion of glycosylphosphatidylinositol-anchored enzyme* Biochim. Biophys. Acta 1564, 473-478

New (1992) *Liposomes: A Practical Approach*

Premkumar et al (2001) *Properties of exogenously added GPI-anchored proteins following their incorporation into cells* J. Cell Biochem. 82, 234-245

Ronzon et al (2004) *Insertion of a glycosylphosphatidylinositol-anchored enzyme into liposomes* J. Membr. Biol. 197, 169-177

Shek and Heath (1983) *Immune response mediated by liposome-associated protein antigens III Immunogenicity of bovine serum albumin covelantly coupled to vesicle surface* Immunology, 50: 101-106

Skountzou et al (2007) *Incorporation of glycosylphosphatidylinositol-anchored granulocyte-macrophage colony-stimulating factor or CD40 ligand enhances immunogenicity of chimeric Simian Immunodeficiency Virus-like particles* J. Virol. 81, 1083-1093

Winger et al (1996) *Lipopeptide conjugates: biomolecular building blocks for receptor activating membrane-mimetic structures* Biomaterials, 17: 437-441

The invention claimed is:

1. A method of quantitatively incorporating an oligopeptide into cell membranes of cells comprising:
dispersing a construct comprising the oligopeptide in water or buffered saline in the absence of organic solvent or detergent; and
contacting the cells with the dispersion of the construct at a concentration and for a time and temperature sufficient to allow the construct to insert into the cell membranes, where the construct is of the structure:

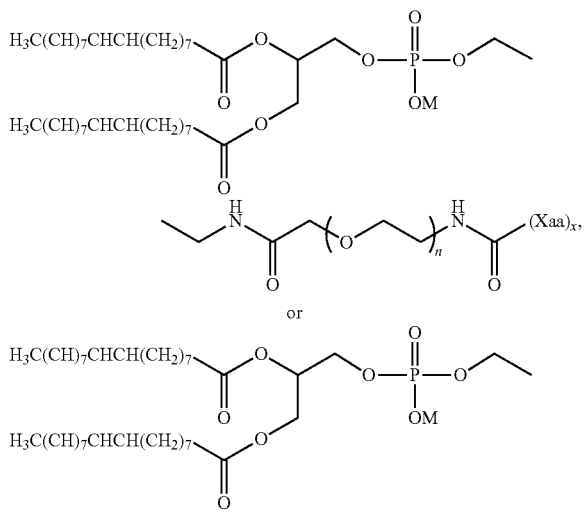

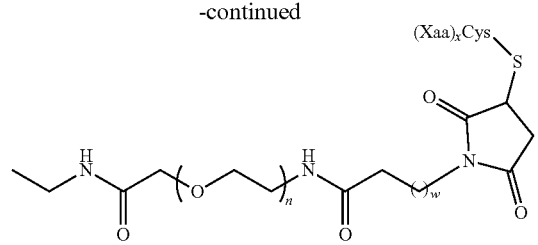

wherein M is a monovalent cation (M+);
n is 6 to 14;
w is 1 or 2;
and
$(Xaa)_x$ is the oligopeptide.

2. The method of claim 1 where the oligopeptide comprises a proximal terminal sequence selected from the group consisting of:

```
SerLysLysLysLysGly;

AlaAlaAlaAla;
and

GlySerGlySerGly.
```

3. The method of claim 1 where the cells are human cells.
4. The method of claim 3 where the cells are red blood cells.
5. The method of claim 4 where the time and temperature is no greater than 2 hours at 37° C. or 24 hours at 4 PC.

* * * * *

SEQUENCE LISTING

```
<160> NUMBER OF SEQ ID NOS: 35

<210> SEQ ID NO 1
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(7)
<223> OTHER INFORMATION: Optional proximal terminal sequence (PTS) of 0
      to 6 residues selected to promote solubility of the peptide

<400> SEQUENCE: 1

Cys Xaa Xaa Xaa Xaa Xaa Xaa Trp Thr Pro Pro Arg Ala Gln Ile Thr
1               5                   10                  15

Gly Tyr Leu Thr Val Gly Leu Thr Arg Arg
            20                  25

<210> SEQ ID NO 2
<211> LENGTH: 27
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(7)
<223> OTHER INFORMATION: Optional proximal terminal sequence (PTS) of 0
      to 6 residues selected to promote solubility of the peptide
```

-continued

```
<400> SEQUENCE: 2

Cys Xaa Xaa Xaa Xaa Xaa Xaa Trp Thr Pro Pro Arg Ala Gln Ile Thr
1               5                   10                  15

Gly Tyr Arg Leu Thr Val Gly Leu Thr Arg Arg
            20                  25

<210> SEQ ID NO 3
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(7)
<223> OTHER INFORMATION: Optional proximal terminal sequence (PTS) of 0
      to 6 residues selected to promote solubility of the peptide

<400> SEQUENCE: 3

Cys Xaa Xaa Xaa Xaa Xaa Xaa Val Met Tyr Ala Ser Ser Gly
1               5                   10

<210> SEQ ID NO 4
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (8)..(13)
<223> OTHER INFORMATION: Optional proximal terminal sequence (PTS) of 0
      to 6 residues selected to promote solubility of the peptide

<400> SEQUENCE: 4

Val Met Tyr Ala Ser Ser Gly Xaa Xaa Xaa Xaa Xaa Xaa Cys
1               5                   10

<210> SEQ ID NO 5
<211> LENGTH: 18
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (12)..(17)
<223> OTHER INFORMATION: Optional proximal terminal sequence (PTS) of 0
      to 6 residues selected to promote solubility of the peptide

<400> SEQUENCE: 5

Asp Tyr His Arg Val Met Tyr Ala Ser Ser Gly Xaa Xaa Xaa Xaa Xaa
1               5                   10                  15

Xaa Cys

<210> SEQ ID NO 6
<211> LENGTH: 19
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (13)..(18)
<223> OTHER INFORMATION: Optional proximal terminal sequence (PTS) of 0
      to 6 residues selected to promote solubility of the peptide
```

```
<400> SEQUENCE: 6

Thr Asn Gly Glu Thr Gly Gln Leu Val His Arg Phe Xaa Xaa Xaa Xaa
1               5                   10                  15

Xaa Xaa Cys

<210> SEQ ID NO 7
<211> LENGTH: 19
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (13)..(18)
<223> OTHER INFORMATION: Optional proximal terminal sequence (PTS) of 0
      to 6 residues selected to promote solubility of the peptide

<400> SEQUENCE: 7

Thr Asn Gly Glu Met Gly Gln Leu Val His Arg Phe Xaa Xaa Xaa Xaa
1               5                   10                  15

Xaa Xaa Ala

<210> SEQ ID NO 8
<211> LENGTH: 20
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (14)..(19)
<223> OTHER INFORMATION: Optional proximal terminal sequence (PTS) of 0
      to 6 residues selected to promote solubility of the peptide

<400> SEQUENCE: 8

Asp Thr Tyr Pro Ala His Thr Ala Asn Glu Val Ser Glu Xaa Xaa Xaa
1               5                   10                  15

Xaa Xaa Xaa Cys
            20

<210> SEQ ID NO 9
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(16)
<223> OTHER INFORMATION: Optional proximal terminal sequence (PTS) of 0
      to 6 residues selected to promote solubility of the peptide

<400> SEQUENCE: 9

Thr Tyr Pro Ala His Thr Ala Asn Glu Val Xaa Xaa Xaa Xaa Xaa Xaa
1               5                   10                  15

Cys

<210> SEQ ID NO 10
<211> LENGTH: 15
<212> TYPE: PRT
<213> ORGANISM: Artificial sequence
<220> FEATURE:
<223> OTHER INFORMATION: Synthetic peptide
```

```
<220> FEATURE:
<221> NAME/KEY: MISC_FEATURE
<222> LOCATION: (9)..(14)
<223> OTHER INFORMATION: Optional proximal terminal sequence (PTS) of 0
      to 6 residues selected to promote solubility of the peptide

<400> SEQUENCE: 10

Pro Ala His Thr Ala Asn Glu Val Xaa Xaa Xaa Xaa Xaa Xaa Cys
1               5                   10                  15

<210> SEQ ID NO 11
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (9)..(14)
<223> OTHER INFORMATION: Optional proximal terminal sequence (PTS) of 0
      to 6 residues selected to promote solubility of the peptide

<400> SEQUENCE: 11

Tyr Pro Ala His Thr Ala Asn Glu Xaa Xaa Xaa Xaa Xaa Xaa Cys
1               5                   10                  15

<210> SEQ ID NO 12
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (9)..(14)
<223> OTHER INFORMATION: Optional proximal terminal sequence (PTS) of 0
      to 6 residues selected to promote solubility of the peptide

<400> SEQUENCE: 12

Thr Tyr Pro Ala His Thr Ala Asn Xaa Xaa Xaa Xaa Xaa Xaa Cys
1               5                   10                  15

<210> SEQ ID NO 13
<211> LENGTH: 16
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (10)..(15)
<223> OTHER INFORMATION: Optional proximal terminal sequence (PTS) of 0
      to 6 residues selected to promote solubility of the peptide

<400> SEQUENCE: 13

Thr Tyr Pro Ala His Thr Ala Asn Glu Xaa Xaa Xaa Xaa Xaa Xaa Cys
1               5                   10                  15

<210> SEQ ID NO 14
<211> LENGTH: 16
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (10)..(15)
<223> OTHER INFORMATION: Optional proximal terminal sequence (PTS) of 0
      to 6 residues selected to promote solubility of the peptide
```

```
<400> SEQUENCE: 14

Tyr Pro Ala His Thr Ala Asn Glu Val Xaa Xaa Xaa Xaa Xaa Xaa Cys
1               5                   10                  15

<210> SEQ ID NO 15
<211> LENGTH: 16
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (10)..(15)
<223> OTHER INFORMATION: Optional proximal terminal sequence (PTS) of 0
      to 6 residues selected to promote solubility of the peptide

<400> SEQUENCE: 15

Pro Ala His Thr Ala Asn Glu Val Ser Xaa Xaa Xaa Xaa Xaa Xaa Cys
1               5                   10                  15

<210> SEQ ID NO 16
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(16)
<223> OTHER INFORMATION: Optional proximal terminal sequence (PTS) of 0
      to 6 residues selected to promote solubility of the peptide

<400> SEQUENCE: 16

Asp Thr Tyr Pro Ala His Thr Ala Asn Glu Xaa Xaa Xaa Xaa Xaa Xaa
1               5                   10                  15

Cys

<210> SEQ ID NO 17
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(16)
<223> OTHER INFORMATION: Optional proximal terminal sequence (PTS) of 0
      to 6 residues selected to promote solubility of the peptide

<400> SEQUENCE: 17

Tyr Pro Ala His Thr Ala Asn Glu Val Ser Xaa Xaa Xaa Xaa Xaa Xaa
1               5                   10                  15

Cys

<210> SEQ ID NO 18
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(16)
<223> OTHER INFORMATION: Optional proximal terminal sequence (PTS) of 0
      to 6 residues selected to promote solubility of the peptide
```

<400> SEQUENCE: 18

Ser Gln Thr Asn Asp Lys His Lys Arg Asp Xaa Xaa Xaa Xaa Xaa Xaa
1               5                   10                  15

Cys

<210> SEQ ID NO 19
<211> LENGTH: 18
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (12)..(17)
<223> OTHER INFORMATION: Optional proximal terminal sequence (PTS) of 0
      to 6 residues selected to promote solubility of the peptide

<400> SEQUENCE: 19

Gln Thr Asn Asp Lys His Lys Arg Asp Thr Tyr Xaa Xaa Xaa Xaa Xaa
1               5                   10                  15

Xaa Cys

<210> SEQ ID NO 20
<211> LENGTH: 31
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (25)..(30)
<223> OTHER INFORMATION: Optional proximal terminal sequence (PTS) of 0
      to 6 residues selected to promote solubility of the peptide

<400> SEQUENCE: 20

Gln Thr Asn Asp Lys His Lys Arg Asp Thr Tyr Ser Ser Gln Thr Asn
1               5                   10                  15

Asp Met His Lys Arg Asp Thr Tyr Xaa Xaa Xaa Xaa Xaa Xaa Cys
                20                  25                  30

<210> SEQ ID NO 21
<211> LENGTH: 18
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (12)..(17)
<223> OTHER INFORMATION: Optional proximal terminal sequence (PTS) of 0
      to 6 residues selected to promote solubility of the peptide

<400> SEQUENCE: 21

Gln Thr Asn Asp Met His Lys Arg Asp Thr Tyr Xaa Xaa Xaa Xaa Xaa
1               5                   10                  15

Xaa Cys

<210> SEQ ID NO 22
<211> LENGTH: 17
<212> TYPE: PRT
<213> ORGANISM: Artificial sequence
<220> FEATURE:
<223> OTHER INFORMATION: Synthetic peptide

```
<220> FEATURE:
<221> NAME/KEY: MISC_FEATURE
<222> LOCATION: (11)..(16)
<223> OTHER INFORMATION: Optional proximal terminal sequence (PTS) of 0
      to 6 residues selected to promote solubility of the peptide

<400> SEQUENCE: 22

Ser Ser Gln Thr Asn Asp Lys His Lys Arg Xaa Xaa Xaa Xaa Xaa Xaa
1               5                   10                  15

Cys

<210> SEQ ID NO 23
<211> LENGTH: 20
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (14)..(19)
<223> OTHER INFORMATION: Optional proximal terminal sequence (PTS) of 0
      to 6 residues selected to promote solubility of the peptide

<400> SEQUENCE: 23

Ser Ser Gln Thr Asn Asp Lys His Lys Arg Asp Thr Tyr Xaa Xaa Xaa
1               5                   10                  15

Xaa Xaa Xaa Cys
            20

<210> SEQ ID NO 24
<211> LENGTH: 20
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (14)..(19)
<223> OTHER INFORMATION: Optional proximal terminal sequence (PTS) of 0
      to 6 residues selected to promote solubility of the peptide

<400> SEQUENCE: 24

Ser Ser Gln Thr Asn Asp Met His Lys Arg Asp Thr Tyr Xaa Xaa Xaa
1               5                   10                  15

Xaa Xaa Xaa Cys
            20

<210> SEQ ID NO 25
<211> LENGTH: 33
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (27)..(32)
<223> OTHER INFORMATION: Optional proximal terminal sequence (PTS) of 0
      to 6 residues selected to promote solubility of the peptide

<400> SEQUENCE: 25

Ser Ser Gln Thr Asn Asp Lys His Lys Arg Asp Thr Tyr Ser Ser Gln
1               5                   10                  15

Thr Asn Asp Met His Lys Arg Asp Thr Tyr Xaa Xaa Xaa Xaa Xaa Xaa
                20                  25                  30

Cys
```

```
<210> SEQ ID NO 26
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(16)
<223> OTHER INFORMATION: Optional proximal terminal sequence (PTS) of 0
      to 6 residues selected to promote solubility of the peptide

<400> SEQUENCE: 26

Gln Thr Asn Asp Lys His Lys Arg Asp Thr Xaa Xaa Xaa Xaa Xaa Xaa
1               5                   10                  15

Cys

<210> SEQ ID NO 27
<211> LENGTH: 18
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (12)..(17)
<223> OTHER INFORMATION: Optional proximal terminal sequence (PTS) of 0
      to 6 residues selected to promote solubility of the peptide

<400> SEQUENCE: 27

Ser Gln Thr Asn Asp Lys His Lys Arg Asp Thr Xaa Xaa Xaa Xaa Xaa
1               5                   10                  15

Xaa Cys

<210> SEQ ID NO 28
<211> LENGTH: 18
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (12)..(17)
<223> OTHER INFORMATION: Optional proximal terminal sequence (PTS) of 0
      to 6 residues selected to promote solubility of the peptide

<400> SEQUENCE: 28

Thr Asn Asp Lys His Lys Arg Asp Thr Tyr Pro Xaa Xaa Xaa Xaa Xaa
1               5                   10                  15

Xaa Cys

<210> SEQ ID NO 29
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(16)
<223> OTHER INFORMATION: Optional proximal terminal sequence (PTS) of 0
      to 6 residues selected to promote solubility of the peptide

<400> SEQUENCE: 29

Glu Glu Thr Gly Glu Thr Gly Gln Leu Val Xaa Xaa Xaa Xaa Xaa Xaa
1               5                   10                  15

Cys
```

```
<210> SEQ ID NO 30
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(16)
<223> OTHER INFORMATION: Optional proximal terminal sequence (PTS) of 0
      to 6 residues selected to promote solubility of the peptide

<400> SEQUENCE: 30

Glu Glu Glu Thr Gly Glu Thr Gly Gln Leu Xaa Xaa Xaa Xaa Xaa Xaa
1               5                   10                  15

Cys

<210> SEQ ID NO 31
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(16)
<223> OTHER INFORMATION: Optional proximal terminal sequence (PTS) of 0
      to 6 residues selected to promote solubility of the peptide

<400> SEQUENCE: 31

Glu Thr Gly Glu Thr Gly Gln Leu Val His Xaa Xaa Xaa Xaa Xaa Xaa
1               5                   10                  15

Cys

<210> SEQ ID NO 32
<211> LENGTH: 16
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (10)..(15)
<223> OTHER INFORMATION: Optional proximal terminal sequence (PTS) of 0
      to 6 residues selected to promote solubility of the peptide

<400> SEQUENCE: 32

Ser Pro Pro Arg Arg Ala Arg Val Thr Xaa Xaa Xaa Xaa Xaa Xaa Cys
1               5                   10                  15

<210> SEQ ID NO 33
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (17)..(22)
<223> OTHER INFORMATION: Optional proximal terminal sequence (PTS) of 0
      to 6 residues selected to promote solubility of the peptide

<400> SEQUENCE: 33

Tyr Arg Tyr Arg Tyr Thr Pro Lys Glu Lys Thr Gly Pro Met Lys Glu
1               5                   10                  15

Xaa Xaa Xaa Xaa Xaa Xaa Cys
            20
```

```
<210> SEQ ID NO 34
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (9)..(14)
<223> OTHER INFORMATION: Optional proximal terminal sequence (PTS) of 0
      to 6 residues selected to promote solubility of the peptide

<400> SEQUENCE: 34

Trp Gln Pro Pro Arg Ala Arg Ile Xaa Xaa Xaa Xaa Xaa Xaa Cys
1               5                   10                  15

<210> SEQ ID NO 35
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(16)
<223> OTHER INFORMATION: Optional proximal terminal sequence (PTS) of 0
      to 6 residues selected to promote solubility of the peptide

<400> SEQUENCE: 35

Thr Ile Thr Gly Leu Glu Pro Gly Thr Glu Xaa Xaa Xaa Xaa Xaa Xaa
1               5                   10                  15

Cys
```